(12) United States Patent
Rajan et al.

(10) Patent No.: US 8,258,169 B2
(45) Date of Patent: Sep. 4, 2012

(54) PYRAZOLE-4-N-ALKOXYCARBOXAMIDES AS MICROBIOCIDES

(75) Inventors: Ramya Rajan, Goa (IN); Harald Walter, Stein (CH); Daniel Stierli, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 13/132,773

(22) PCT Filed: Dec. 1, 2009

(86) PCT No.: PCT/EP2009/066119
§ 371 (c)(1),
(2), (4) Date: Jun. 3, 2011

(87) PCT Pub. No.: WO2010/063700
PCT Pub. Date: Jun. 10, 2010

(65) Prior Publication Data
US 2011/0230537 A1    Sep. 22, 2011

(30) Foreign Application Priority Data
Dec. 5, 2008    (IN) .......................... 2764/DEL/2008

(51) Int. Cl.
*A61K 31/415*    (2006.01)
*C07D 231/10*    (2006.01)
(52) U.S. Cl. ..................................... 514/406; 548/374.1
(58) Field of Classification Search .................. 514/406; 548/374.1
See application file for complete search history.

(56) References Cited

U.S. PATENT DOCUMENTS
| | | | |
|---|---|---|---|
| 3,118,933 A | 1/1964 | Wolf et al. | |
| 6,777,440 B2 | 8/2004 | Walker et al. | |
| 2005/0182032 A1 | 8/2005 | Nagasawa et al. | |

FOREIGN PATENT DOCUMENTS
| | | |
|---|---|---|
| DE | 1182244 | 11/1964 |
| JP | 48072138 | 9/1973 |
| WO | 2006016708 | 2/2006 |
| WO | 2007141009 | 12/2007 |

OTHER PUBLICATIONS

S.W. Baldwin, R.B. McFadyen, J. Aube, J.D. Wilson: "Diastereoselectivity in the intramolecular cycloaddition reactions of nitrones derived from 5-alkenales and chiral hydroxylamines" Tetrahedron Letters, vol. 32, No. 35, Jan. 1, 1991, pp. 4431-4434.

Kabalka, G.W. et al: "Selected reductions of conjugated nitroalkenes" Tetrahedron, Elsevier Science Publishers, Amsterdam, NL, vol. 46, No. 21, Jan. 1, 1990, pp. 7443-7457.

F.J. Kokko, P. Beak: "The electrophilic amination of organolithiums with methyllithium complexes of N-substituted methoxyamines", Tetrahedron Letters, vol. 24, No. 6, Mar. 1, 1983, pp. 561-564.

A.H. Beckett, K. Haya, G.R. Jones, P.H. Morgan: "Synthetic routes to optical isomers of primary and secondary hydroxylamines of 1-arylisopropylamines" Tetrahedron, vol. 31, Jan. 1, 1975, pp. 1531-1535.

R.T. Gilsdorf, F.F. Nord: "Reverse addition of lithium aluminum hydride to nitroolefins" Journal of the American Chemical Society, vol. 74, No. 7, Apr. 5, 1952, pp. 1837-1843.

S.M. Bakunova, I.A. Grigor'ev, I.A. Kirilyuk, Yu.V. Gatilov, I. Yu. Bagryanskaya and L.B. Volodarskii: "Synthesis of stable oxazolidine nitroxyl radicals with methoxy groups at the alpha-carbon atoms to the radical site" Russian Chemical Bulletin, vol. 41, No. 4, Apr. 1, 1992, pp. 758-764.

Miyagishima, T. et al: "Further Studies on Synthesis and Antimicrobial Activity of Thioformin Analogues" Chemical and Pharmaceutical Bulletin, Pharmaceutical Society of Japan, Tokyo, JP, vol. 22, No. 10, Jan. 1, 1974, pp. 2283-2287.

F. Benington, R.D. Morin, L.C. Clark Jr.: "Behavioral and Neuropharmacological Actions of N-Aralkylhydroxylamines and Their O-Methyl Ethers" Journal of Medicinal Chemistry, vol. 8, No. 1, Jan. 1, 1965, pp. 100-104.

*Primary Examiner* — Rebecca Anderson
*Assistant Examiner* — Samantha Shterengarts
(74) *Attorney, Agent, or Firm* — Kody Jones

(57) ABSTRACT

Compounds of formula (I) in which the substituents are as defined in claim 1, are suitable for use as microbiocides.

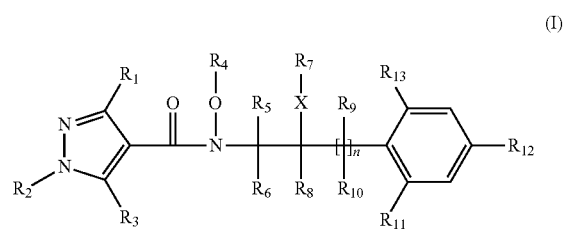

14 Claims, No Drawings

PYRAZOLE-4-N-ALKOXYCARBOXAMIDES AS MICROBIOCIDES

This application is a 371 of International Application No. PCT/EP2009/066119 filed Dec. 1, 2009, which claims priority to IN 2764/DEL/2008 filed Dec. 5, 2008, the contents of which are incorporated herein by reference.

The present invention relates to novel microbiocidally active, in particular fungicidally active, carboxamides. It further relates to intermediates used in the preparation of these compounds, to compositions which comprise these compounds and to their use in agriculture or horticulture for controlling or preventing infestation of plants by phytopathogenic microorganisms, preferably fungi.

Fungicidally active carboxamides are described in EP 1787981 and EP 1792901.

It has been found that novel carboxamides with a specific substitution pattern have microbiocidal activity.

The present invention accordingly relates to N-alkoxycarboxamides of formula I

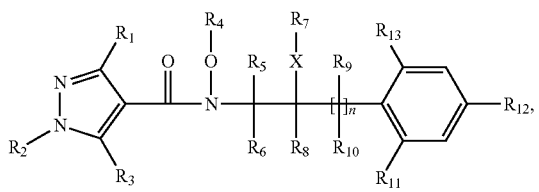

(I)

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$, $R_6$, $R_8$, $R_9$ and $R_{10}$ are, independently from each other, hydrogen, halogen, $C_1$-$C_4$alkyl or $C_1$-$C_4$haloalkyl;
$R_7$ is hydrogen, halogen, $C_1$-$C_4$alkyl, $C_2$-$C_6$alkenyl or $C_3$-$C_6$alkinyl;
$R_{11}$ is hydrogen, halogen or $C_1$-$C_6$alkyl;
$R_{12}$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C(C_1$-$C_4$alkyl)=NO—$C_1$-$C_4$alkyl, $C_1$-$C_6$haloalkyl,
$C_1$-$C_6$haloalkoxy, $C_2$-$C_6$haloalkenyl, or $C_2$-$C_6$haloalkenyloxy;
$R_{13}$ is hydrogen, halogen, $C_1$-$C_6$alkyl;
X is oxygen, sulfur or absent; with the proviso that $R_7$ is different from halogen if X is oxygen or sulfur; and
n is 0 or 1; and agronomically acceptable salts/isomers/structural isomers/stereoisomers/diastereoisomers/enantio-mers/tautomers and N-oxides of those compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups can be mono- or di-unsaturated. The cycloalkyl groups occurring in the definitions of the substituents are, for example, cyclopropyl, cyclobutyl, cyclopentyl or cyclohexyl. Halogen is generally fluorine, chlorine, bromine or iodine, preferably fluorine, bromine or chlorine. This also applies, correspondingly, to halogen in combination with other meanings, such as halogenalkyl or halogenalkoxy. Haloalkyl groups preferably have a chain length of from 1 to 4 carbon atoms. Halonalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

In preferred compounds of formula I, independently from each other,
a) $R_1$ is difluoromethyl, trifluoromethyl or methyl,
b) $R_2$ is methyl;
c) $R_3$ is hydrogen or fluoro;
d) $R_4$ is hydrogen, methyl or ethyl;
e) $R_4$ is methyl;
f) $R_5$ is hydrogen or methyl;
g) n is 0;
h) X is oxygen;
i) $R_8$, $R_9$ and $R_{10}$ are hydrogen;
j) $R_{11}$, $R_{12}$ and $R_{13}$ is hydrogen or chloro;
k) $R_{12}$ is chloro or $C_1$-$C_4$alkyl;
l) $R_6$ is hydrogen and
m) $R_7$ is methyl.

Especially preferred compounds of formula I are those, wherein
$R_1$ is difluoromethyl or trifluoromethyl;
$R_2$ is methyl;
$R_3$ is hydrogen;
$R_4$ is methyl;
$R_{11}$, $R_{12}$ and $R_{13}$ are, independently from each other, hydrogen or halogen, preferably hydrogen or chlorine.

Further compounds of formula I are preferred, wherein X is oxygen and simultaneously $R_7$ is $C_1$-$C_4$alkyl, preferably methyl; or X is absent and $R_7$ is hydrogen.

Compounds of formula I may be prepared by reacting a compound of formula II

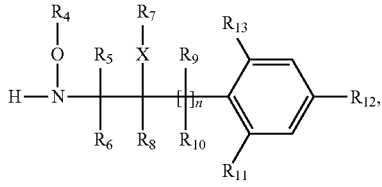

(II)

wherein $R_4$, $R_5$, $R_6$, $R_7$, X, $R_8$, $R_9$, $R_{10}$, n, $R_{11}$, $R_{12}$ and $R_{13}$ are as defined under formula I; with a compound of formula III

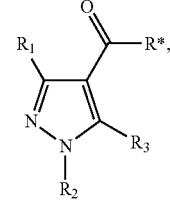

(III)

in which $R_1$, $R_2$ and $R_3$ are as defined under formula I, and R* is halogen, hydroxy or $C_{1-6}$ alkoxy, preferably chloro.

The reactions to give compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

When R* is hydroxy, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI), may be used.

The intermediates of the formula II

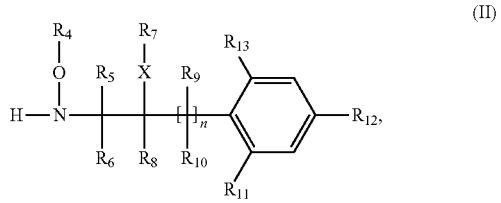

(II)

wherein $R_4$, $R_5$, $R_6$, $R_7$, X, $R_8$, $R_9$, $R_{10}$, n, $R_{11}$, $R_{12}$ and $R_{13}$ are as defined under formula I, preferably wherein $R_4$ is $C_1$-$C_4$alkyl; are novel and were developed specifically for the preparation of the compounds of the formula I. Accordingly, these intermediates of the formula II also form a part of the subject-matter of the present invention.

The preferred substituent definitions for the compounds of formula I are also valid for the compound of formula II. Thus, preferred compounds of formula II are those, wherein, independently from each other, a) $R_4$ is hydrogen, methyl or ethyl; especially preferred methyl;

b) $R_5$ is hydrogen or methyl;

c) n is 0;

d) X is oxygen;

e) $R_8$, $R_9$ and $R_{10}$ are hydrogen;

f) $R_{11}$, $R_{12}$ and $R_{13}$ is hydrogen or chloro;

g) $R_{12}$ is chloro or $C_1$-$C_4$alkyl;

h) $R_6$ is hydrogen and i) $R_7$ is methyl.

Intermediates of Formula IIA

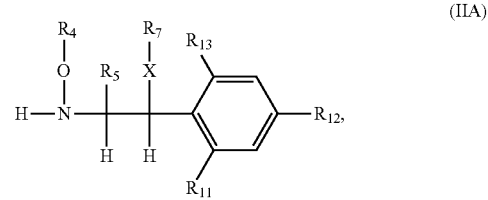

(IIA)

wherein $R_4$, $R_5$, X, $R_7$, $R_{11}$, $R_{12}$ and $R_{13}$ are as defined under formula I may be prepared as described in reaction scheme 1.

Scheme 1:

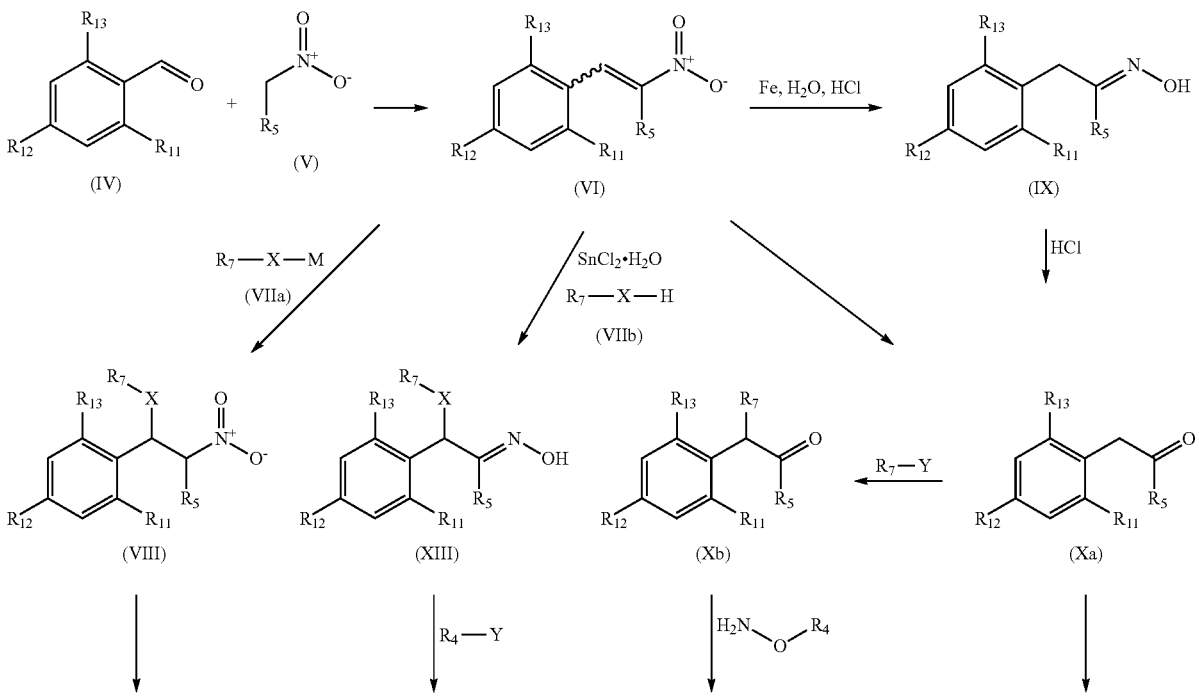

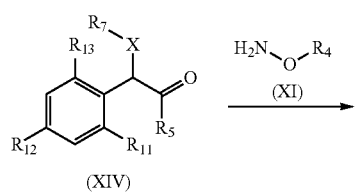 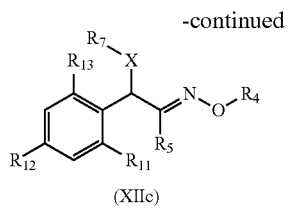 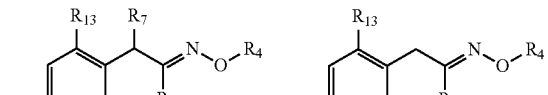

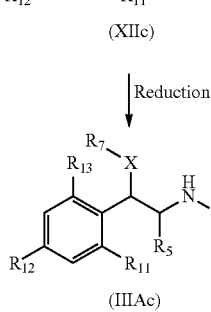 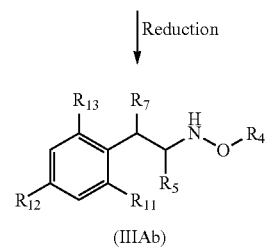 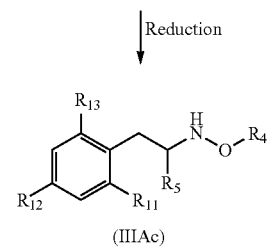

Nitroalkenes of formula VI, in which and $R_5$, $R_{11}$, $R_{12}$ and $R_{13}$ are as defined under formula IIA, can be prepared by a Henry-reaction (nitroaldol-reaction) of a nitroalkane of formula V, in which $R_5$ is as defined under formula IIA, with a carbonyl compound of formula (IV), in which $R_{11}$, $R_{12}$ and $R_{13}$ are as defined under formula IIA, in the presence of acetic acid and ammonium acetate at temperatures between ambient temperature and reflux temperature. Michael addition of a compound of formula VIIa, in which $R_7$ and X are as defined under formula I and M is Li, Na, K or hydrogen, to the nitroalkenes of formula VI may be accomplished using earth alkali alcoholates preferred sodium, potassium and lithium salts in the corresponding alcohol, thiol, toluene or an ether solvent such as diethyl ether, ethylene glycol dimethyl ether, diethylene glycol dimethyl ether, tetrahydrofuran or dioxane to form the nitroalkanes of formula VIII, in which $R_5$, $R_7$, $R_{11}$, $R_{12}$ and $R_{13}$ are as defined under formula IIA.

Nitroalkenes of formula VI, in which and $R_5$, $R_{11}$, $R_{12}$ and $R_{13}$ are as defined under formula IIA, may be reduced with iron and hydrochloric acid to give oximes of formula IX, in which $R_5$, $R_{11}$, $R_{12}$ and $R_{13}$ are as defined under formula IIA. Said oximes can be hydrolyzed to ketones of formula Xa, in which $R_5$, $R_{11}$, $R_{12}$ and $R_{13}$ are as defined under formula IIA, as it is described, for example, in M. Kulka and H. Hibbert *J. Am. Chem. Soc.* 65, 1180 (1943) and in Prasun K. Pradhan et al. *Synthetic Commun.*, 35, 913-922, 2005. The reaction is carried out at temperatures of between 40-100° C. in a convenient organic solvent such as methanol, ethanol, tert-butanol, trifluoroethanol or dioxane.

Alkylation of ketones of formula Xa with a compound $R_7$—Y, in which $R_7$ is as defined under formula IIA and Y represents a leaving group, such as halogen, mesylate or tosylate, in the presence of a base yields an α-alkylated ketone of formula Xb, wherein $R_5$, $R_7$, $R_{11}$, $R_{12}$ and $R_{13}$ are as defined under formula IIA. The alkylation reaction is advantageously carried out in aprotic inert organic solvents. Such solvents are hydrocarbons such as benzene, toluene, xylene or cyclohexane, ethers such as diethyl ether, ethylene glycol dimethyl ether, diethylene glycol dimethyl ether, tetrahydrofuran or dioxane, amides such as N,N-dimethylformamide, diethylformamide or N-methylpyrrolidinone. The reaction temperatures are between −20° C. and +120° C. Suitable bases are inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example crown ether, in particular 18-crown-6, or a tetraalkylammonium salt.

O-alkoxy oxime derivatives of formula XIIa, XIIb may be prepared by oximation of ketones of formula Xa and Xb with O-alkyl hydroxylamine derivatives of formula XI or a salt thereof. Suitable solvents carrying out the oximation step are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide, N-methylpyrrolidinone water or mixtures. The reaction temperatures are advantageously between −20° C. and +120° C. In general, the reactions can be carried out at ambient temperature. Suitable bases are, in particular pyridine, tertiary amines such as trimethylamine, triethylamine, quinuclidine, 1,4-diazabicyclo [2.2.2]octane, 1,5-diazabicyclo[4.3.0]non-5-ene or 1,5-diazabicyclo[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases.

Oxime derivatives of formula XIII may be prepared by selective reduction of nitroalkenes of formula VI in an alcohol or thiol of formula VIIb using $SnCl_2.2H_2O$ according the procedure reported by R. S. Varma and G. W. Kabalka *Chem. Lett.*, 243-244 (1985). Oxime ether derivatives of formula XIIc may be prepared by O-alkylation of oxime derivatives of formula XIII with a compound $R_4$—Y, in which $R_4$ is as defined under formula IIA and Y represents a leaving group, such as halogen, mesylate or tosylate, in the presence of a base. Alternatively oxime ether derivatives of formula XIIc may also be prepared by oximation of a ketone of formula XIV with O-alkyl hydroxylamine derivatives of formula XI or a salt thereof.

Ketones of formula XIV may be prepared by conversion of nitroalkanes of formula VIII, by Nef reaction according to the procedure described by J. M Aizpurua and C. Palomo *THL*, Vol. 28, No. 44, pp 5361-5364 (1987).

O-Alkylhydroxylamines of formula IIAa, IIAb and IIAc may be prepared by the reduction of O-alkoxy oxime derivatives of formula XIIa, XIIb and XIIc.

Intermediates of Formula IIA

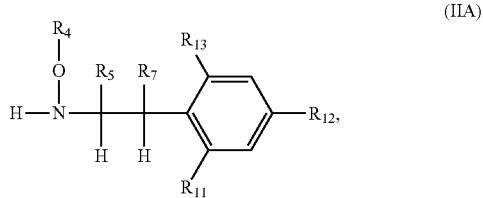

(IIA)

wherein $R_4$, $R_5$, $R_7$, $R_{11}$, $R_{12}$ and $R_{13}$ are as defined under formula I may be prepared as described in reaction scheme 2.

α-alkylated arylacetate derivatives of the formula XVI, can be synthesized by the alkylation of an arylacetate derivative of formula XV, with an halide, such as $R_7$—Y, wherein $R_7$ is as defined under formula IIA and Y represents a leaving group, such as halogen, mesylate or tosylate, in the presence of a base. The compound of formula XVI is hydrolyzed by a hydroxide, such as LiOH. The resultant acid of the formula XVII, can then be converted to the corresponding acylchloride and this acylchloride can then in situ be reacted with N,O-dimethylhydroxylamine to afford a Weinreb amide of formula XVIII, in which $R_7$, $R_{11}$, $R_{12}$ and $R_{13}$ are as defined under formula IIA. A subsequent reaction with a Grignard reagent of the formula $R_5$—MgBr, wherein $R_5$ is as defined under formula IIA, yields the ketone of formula Xb, which can be converted to a compound of formula IIAb by reactions described in scheme 1.

Aldehyde derivatives of formula Xb1 may be prepared by the partial reduction of a Weinreb amide of formula XVIII with LiAlH₄, or DIBAL-H.

Scheme 2:

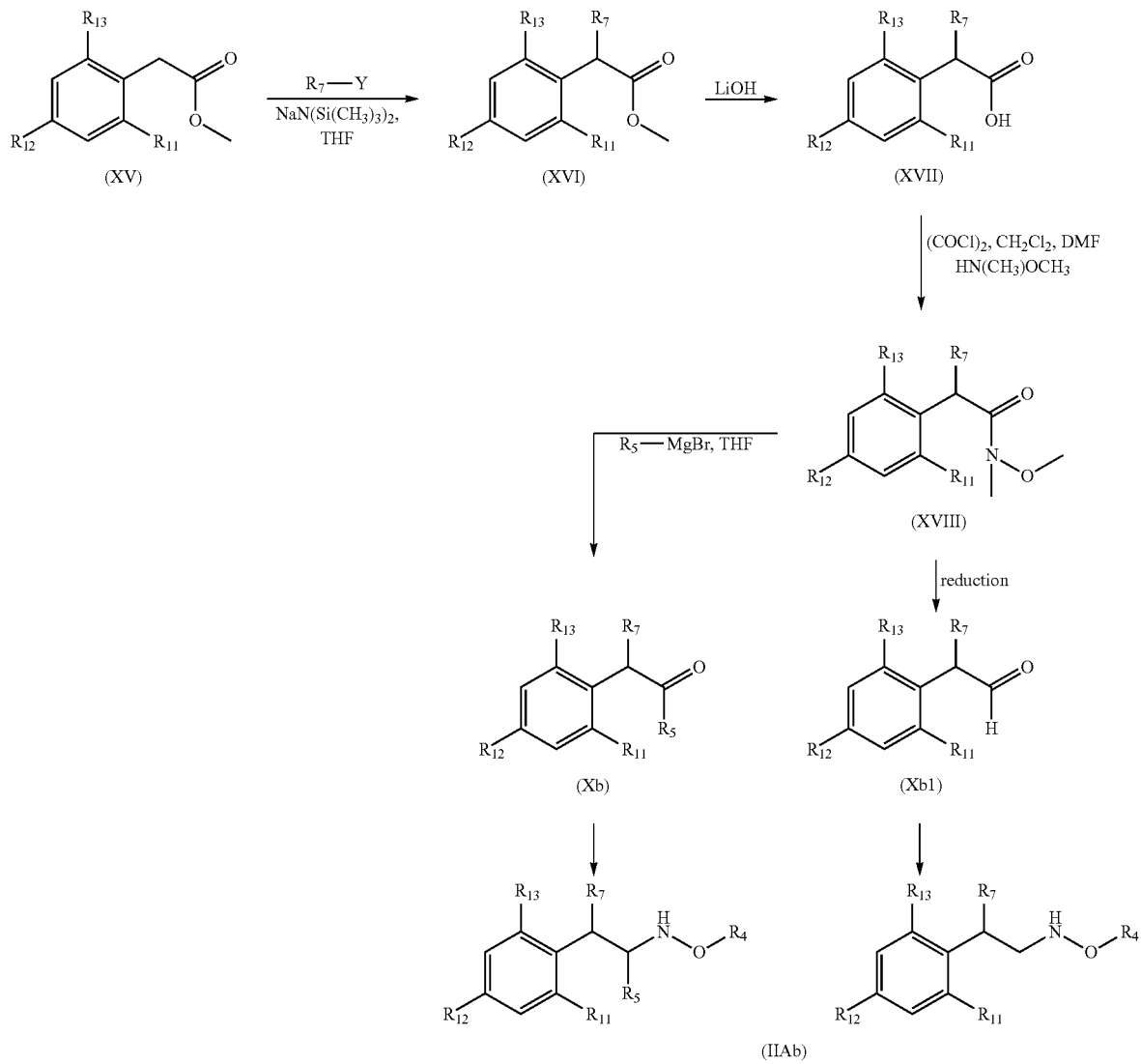

Intermediates of Formula IIA

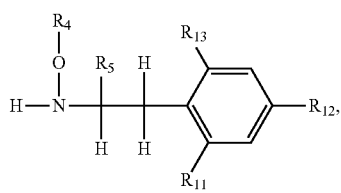
(IIA)

wherein $R_4$, $R_5$, $R_{11}$, $R_{12}$ and $R_{13}$ are as defined under formula I may be prepared as described in reaction scheme 3.

Scheme 3:

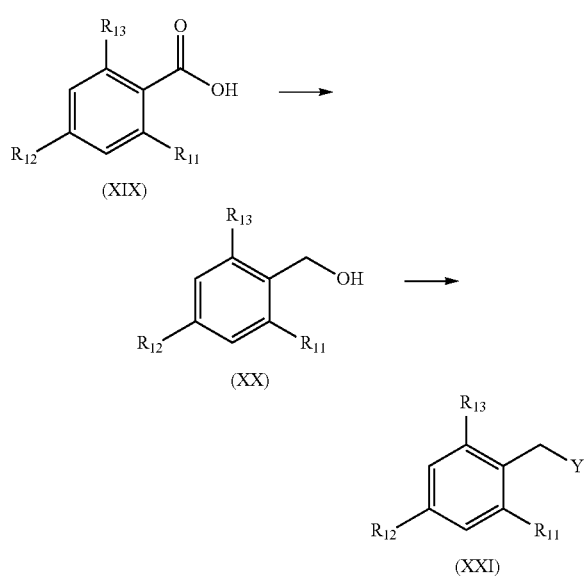

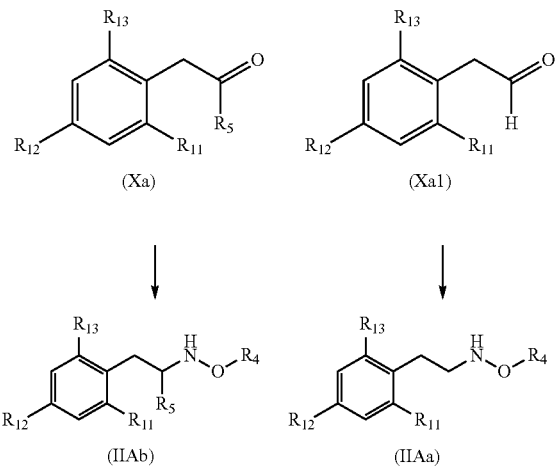

Aldehyde derivatives of formula Xa1 can be prepared according to methods known in the art by reduction of acid derivatives of formula XIX into alcohol derivative of formula XX followed by the transformation into activated benzylic derivative of formula XXI, transformation into nitrile derivative of formula XXII followed by reduction into aldehyde derivative of formula Xa1, described in the preparation section. A subsequent reaction of nitrile derivative of formula XXII with a Grignard reagent of the formula $R_5$—MgBr, wherein $R_5$ is as defined under formula IIA, yields the ketone of formula Xa, which can be converted to a compound of formula IIAb by reactions as described in scheme 1.

Intermediates of Formula IIB

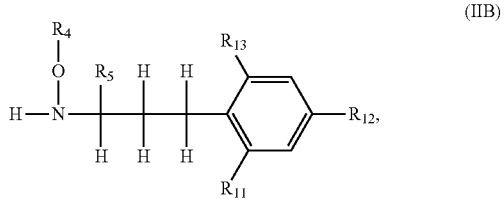
(IIB)

wherein $R_4$, $R_5$, $R_{11}$, $R_{12}$ and $R_{13}$ are as defined under formula I may be prepared as described in reaction scheme 4.

Scheme 4:

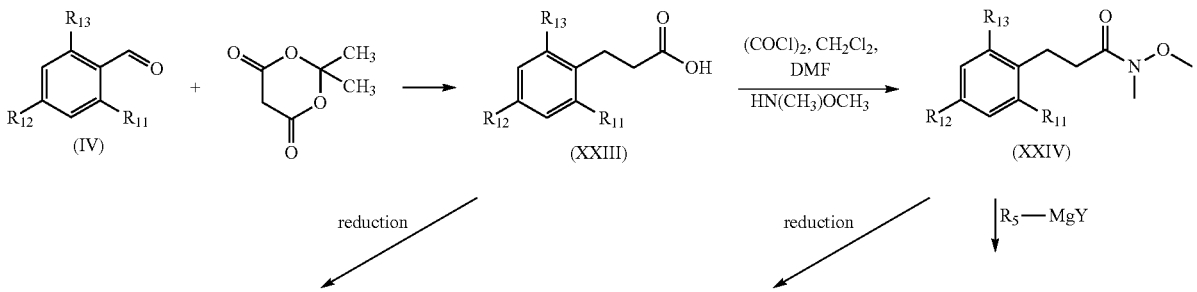

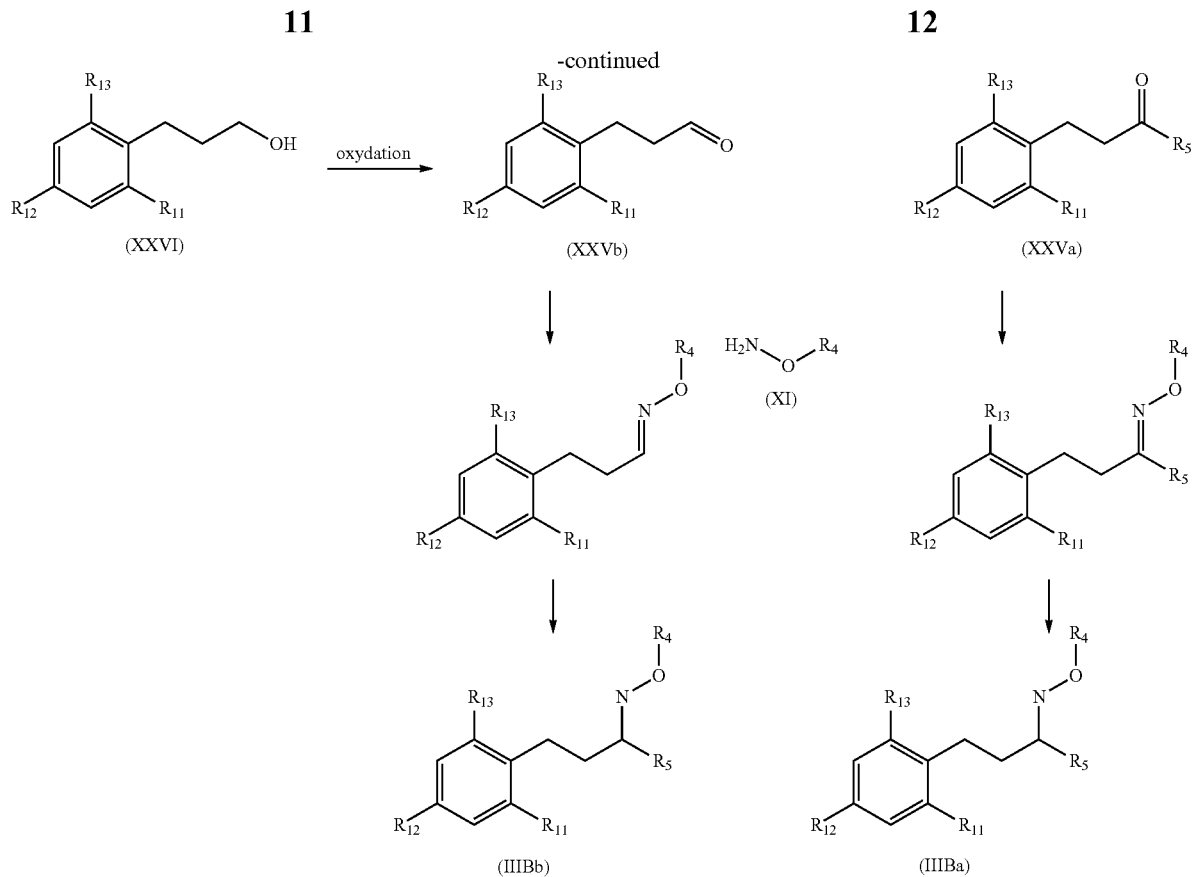

The aldehyde of formula IV can be converted with Meldrum's acid and triethylammonium formate to the corresponding acid of formula XXIII, as it is described, for example, by G. Toth et. al. in *Synth. Commun.* 25 (19), 3067-3074 (1995). Said acid can be converted to the corresponding acylchloride and this acylchloride can then in situ be reacted with N,O-dimethylhydroxylamine to afford a Weinreb amide of formula XXIV. Subsequent reaction of the Weinreb amide of formula XXIV with a Grignard reagent of the formula $R_5$—MgY, wherein $R_5$ is as defined under formula IIA, yields the ketone of formula XXVa.

Aldehyde of formula XXVb may be prepared by the partial reduction of Weinreb amide of formula XXIV with $LiAlH_4$, or DIBAL-H. Alternatively said aldehyde may be prepared by oxidation of alcohol of formula XXVI. Suitable oxidation reagents include pyridinium chlorochromate (PCC), Swern reagent (oxalylchloride/DMSO), Dess-Martin Periodinane and $MnO_2$. Suitable solvents include dichloromethane and THF. The reaction temperature typically lies in the range of −50° C. to 20° C.

Ketone and aldehyde derivatives of formula XXVa and XXVb can be further converted to compounds of formula IIBa and IIBb by reactions as described in scheme 1.

Intermediates of Formula IIB

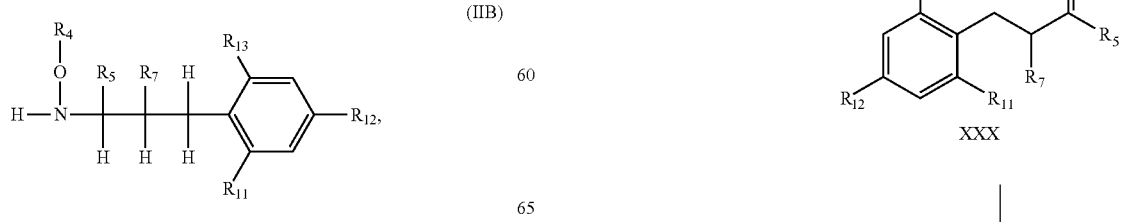

wherein $R_4$, $R_5$, $R_7$, $R_{11}$, $R_{12}$ and $R_{13}$ are as defined under formula I may be prepared as described in reaction scheme 5.

Scheme 5:

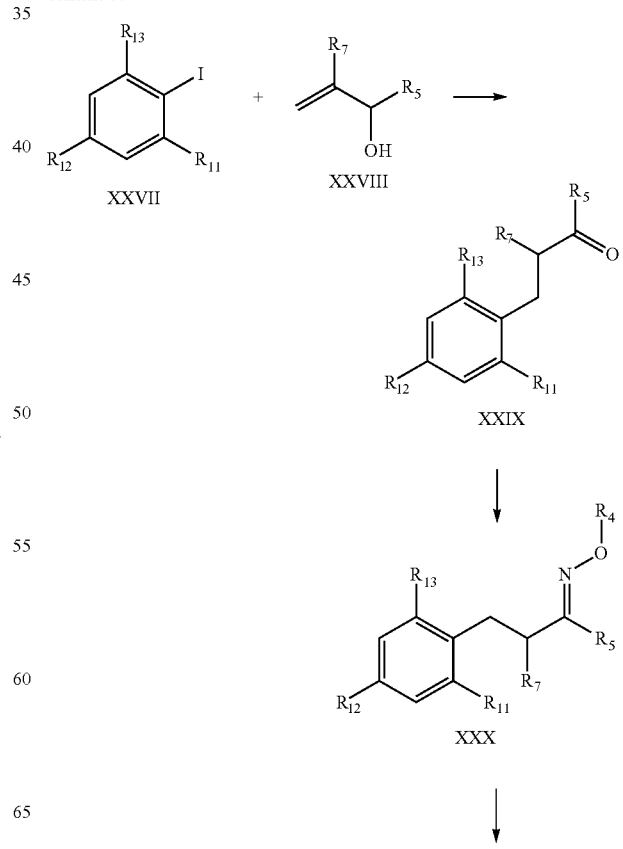

-continued

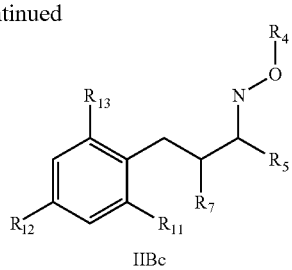

IIBc

Ketone or aldehyde derivatives of formula XXIX may be prepared by the palladium-catalyzed arylation of allylic alcohols of formula XXVIII with aryliodides of formula XXVII in water as described for example by Hong Zhao, Ming-Zhong Cai et. al. in *Synth. Commun.* 31 (23), 3665-3669 (2001); Alberto Scrivanti, Ugo Matteoli et. al. in *Tetrahedron* 64, 543-548 (2008). Ketone and aldehyde derivatives of formula XXIX can be further converted to compounds of formula IIBc by reactions described in scheme 1.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB (b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus*, *A. flavus*, *A. terrus*, *A. nidulans* and *A. niger*, those causing Blastomycosis such as *Blastomyces dermatitidis*; those causing Candidiasis such as *Candida albicans*, *C. glabrata*, *C. tropicalis*, *C. parapsilosis*, *C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera*, *Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid [2-(4-chloro-phenyl)-1-methyl-ethyl]-methoxy-amide (compound 1.001)

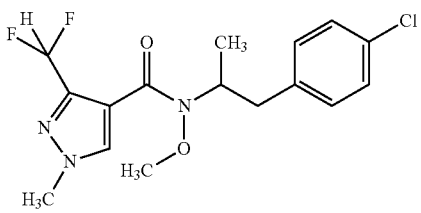

A solution of 3-difluoromethyl-1-methyl-1H-pyrazole-4-carbonyl chloride (564 mg; 2.9 mmol) in dichloromethane (5 ml) was added dropwise to a stirred solution of N-[2-(4-chloro-phenyl)-1-methyl-ethyl]-O-methyl-hydroxylamine (600 mg; 2.9 mmol), prepared as described in example P13, triethylamine (0.80 ml; 5.8 mmol) in dichloromethane (10 ml) at 0° C. The reaction mixture was stirred for 6 hours at ambient temperature. The reaction mixture was washed with 1M NaOH (20 ml), 1M HCl (20 ml) brine (20 ml) and then dried over $Na_2SO_4$. After removal of the solvent the residue was purified by flash chromatography over silica gel (eluant: c-hexane/ethyl acetate 1:1).

0.99 g (93.4% of theory) of 3-difluoromethyl-1-methyl-1H-pyrazole-4-carboxylic acid [2-(4-chloro-phenyl)-1-methyl-ethyl]-methoxy-amide (compound 1.001) was obtained in form of a resin.

$^1$H NMR: ($CDCl_3$, 400 MHz):
1.33-1.37 (d, 3H); 2.77-2.82 (dd, 1H); 3.07-3.13 (dd, 1H); 3.64 (s, 3H); 3.94 (s, 3H); 4.63-4.68 (m, 1H); 6.98-7.28 (m, 5H); 7.61 (s, 1H).
MS $[M+H]^+$ 358/360.

Example P2

Preparation of 3-difluoromethyl-1-methyl-1H-pyrazole-4-carboxylic acid [2-(2,4-dichlorophenyl)-1-methyl-ethyl]-methoxy-amide (compound 1.002)

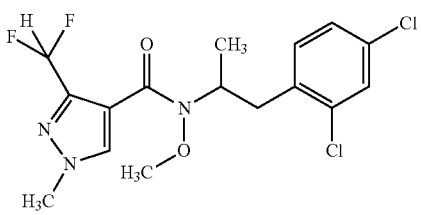

A solution of 3-difluoromethyl-1-methyl-1H-pyrazole-4-carbonyl chloride (0.91 g; 4.7 mmol) in dichloromethane (5 ml) was added dropwise to a stirred solution of N-[2-(2,4-dichlorophenyl)-1-methyl-ethyl]-O-methyl-hydroxylamine (1.0 g; 4.27 mmol), prepared as described in example P14, triethylamine (0.90 ml; 6.4 mmol) in dichloromethane (7 ml) at 0° C. The reaction mixture was stirred for 1.5 hours at ambient temperature. The reaction mixture was washed with 1M NaOH (20 ml), 1M HCl (20 ml) brine (20 ml) and then dried over $Na_2SO_4$. After removal of the solvent the residue was purified by flash chromatography over silica gel (eluant: hexane/ethyl acetate 7:3).

1.35 g (80.3% of theory) of 3-difluoromethyl-1-methyl-1H-pyrazole-4-carboxylic acid [2-(2,4-dichlorophenyl)-1-methyl-ethyl]-methoxy-amide (compound 1.002) was obtained in form of a white solid (m.p. 98-102° C.).

$^1$H NMR: ($CDCl_3$, 400 MHz):

1.41-1.46 (d, 3H); 2.99-3.04 (dd, 1H); 3.17-3.23 (dd, 1H); 3.60 (s, 3H); 3.95 (s, 3H); 4.68-4.70 (m, 1H); 7.10-7.62 (m, 5H).

MS $[M+H]^+$ 392/394/396.

Example P3

Preparation of 3-difluoromethyl-1-methyl-1H-pyrazole-4-carboxylic acid methoxy-[1-methyl-2-(2,4,6-trichlorophenyl)-ethyl]-amide (compound 1.003)

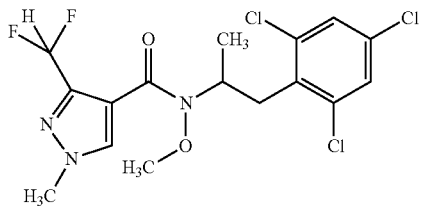

To a solution of O-Methyl-N-[1-methyl-2-(2,4,6-trichlorophenyl)-ethyl]-hydroxylamine (0.65 g, 2.4 mmol) prepared as described in example P15d, in dichloromethane (5 ml) was added triethylamine (0.844 ml, 6.0 mmol) followed by drop wise addition of a solution 3-Difluoromethyl-1-methyl-1H-pyrazole-4-carbonyl chloride (0.519 g, 2.67 mmol) in dichloromethane at 0° C. After complete addition of acid chloride the mixture was stirred 18 hours at ambient temperature. When the TLC confirmed completion of the reaction, the reaction mass was diluted with water and extracted with dichloromethane (3×60 ml). The combined dichloromethane layer were washed with 2N HCl, followed by saturated $NaHCO_3$, then with water and finally with brine solution before drying over sodium sulfate and evaporation of the solvent. The resulting crude mass was purified by column chromatography using 60-120µ mesh silica gel and product collected at 30% ethyl acetate in hexane as eluent to give 3-difluoromethyl-1-methyl-1H-pyrazole-4-carboxylic acid methoxy-[1-methyl-2-(2,4,6-trichloro-phenyl)-ethyl]-amide (0.51 g, 49%) as off white solid. m.p: 110-112° C.

$^1$H NMR (400 MHz, $CDCl_3$): δ 1.38-1.39 (d, 3H), 3.20-3.26 (dd, 1H), 3.32-3.37 (dd, 1H), 3.70 (s, 3H), 3.97 (s, 3H), 4.88-4.93 (m, 1H), 7.02-7.29 (t, 1H), 7.27 (s, 2H), 7.81 (s, 1H)

MS $[M+H]^+$ 426/428/430

Example P4

Preparation of 3-difluoromethyl-1-methyl-1H-pyrazole-4-carboxylic acid{2-[4-(4-chloro-phenoxy)-phenyl]-1-methyl-ethyl}-methoxy-amide (compound 1.015)

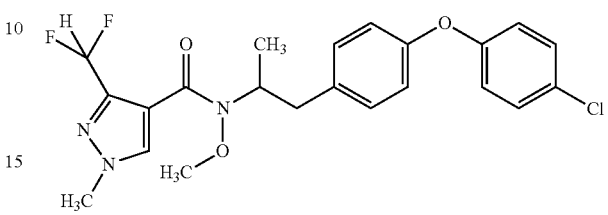

A solution of 3-difluoromethyl-1-methyl-1H-pyrazole-4-carbonyl chloride (797 mg; 4.1 mmol) in dichloromethane (5 ml) was added dropwise to a stirred solution of N-{2-[4-(4-chloro-phenoxy)-phenyl]-1-methyl-ethyl}-O-methyl-hydroxylamine (1.2 g; 4.1 mmol), prepared as described in example P16, triethylamine (1.10 ml; 8.2 mmol) in dichloromethane (10 ml) at 0° C. The reaction mixture was stirred over night at ambient temperature. After removal of the solvent the residue was purified by flash chromatography over silica gel (eluant: c-hexane/ethyl acetate 1:1).

1.2 g (66% of theory) of 3-difluoromethyl-1-methyl-1H-pyrazole-4-carboxylic acid{2-[4-(4-chloro-phenoxy)-phenyl]-1-methyl-ethyl}-methoxy-amide (compound 1.015) was obtained in form of a oil.

$^1$H NMR: ($CDCl_3$, 400 MHz):

1.36-1.39 (d, 3H); 2.78-2.84 (dd, 1H); 3.05-3.12 (dd, 1H); 3.65 (s, 3H); 3.94 (s, 3H); 4.64-4.68 (m, 1H); 6.80-6.90 (m, 4H); 6.95-7.23 (t, 1H, $CHF_2$); 7.17-7.26 (m, 4H); 7.67 (s, 1H).

MS $[M+H]^+$ 450/452.

Example P5

Preparation of 3-difluoromethyl-1-methyl-1H-pyrazole-4-carboxylic acid [2-(2,4-dichlorophenyl)-1-methyl-ethyl]-hydroxy-amide (compound 1.028)

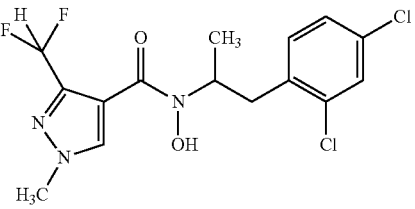

A solution of 3-difluoromethyl-1-methyl-1H-pyrazole-4-carbonyl chloride (2.10 g; 11.0 mmol) in dichloromethane (5 ml) was added dropwise to a stirred suspension of N-[2-(2,4-dichlorophenyl)-1-methyl-ethyl]-hydroxylamine (2.0 g; 9.10 mmol), prepared as described in example P17, triethylamine (3.10 ml; 22 mmol) in dichloromethane (15 ml) at 0° C. The reaction mixture was stirred over night at ambient temperature. The reaction mixture was poured onto 1M HCl (50 ml), extracted with dichloromethane (3×20 ml) and then dried over $Na_2SO_4$. After removal of the solvent the residue (5.08 g) was purified by flash chromatography over silica gel (eluant: c-hexane/ethyl acetate 7:3). 1.51 g (43.8% of theory) of 3-difluoromethyl-1-methyl-1H-pyrazole-4-carboxylic acid [2-

(2,4-dichlorophenyl)-1-methyl-ethyl]-hydroxy-amide (compound 1.028) was obtained in form of a white solid (m.p. 162-167° C.).

$^1$H NMR: (CDCl$_3$, 400 MHz):
1.40-1.41 (d, 3H); 2.89-2.94 (dd, 1H); 3.03-3.14 (dd, 1H); 3.86 (s, 3H); 4.3-4.5 (m$_{br}$, 1H); 6.5-7.0 (m$_{br}$, 2H); 7.19-7.21 (m, 2H); 7.36 (m, 1H); 7.8-8.6 (m$_{br}$, 1H).

MS [M+H]$^+$ 378/380/382.

Example P6

Preparation of 3-difluoromethyl-1-methyl-1H-pyrazole-4-carboxylic acid [2-(2,4-dichlorophenyl)-1-methyl-ethyl]-ethoxy-amide (compound 1.031)

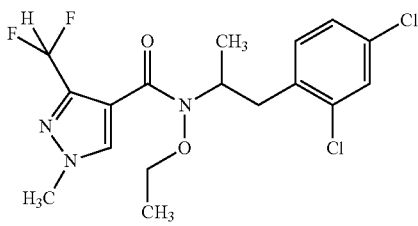

A solution of 3-difluoromethyl-1-methyl-1H-pyrazole-4-carbonyl chloride (0.86 g; 4.4 mmol) in dichloromethane (5 ml) was added dropwise to a stirred solution of N-[2-(2,4-dichlorophenyl)-1-methyl-ethyl]-O-ethyl-hydroxylamine (1.0 g; 4.0 mmol), prepared as described in example P18, triethylamine (0.82 ml; 6.0 mmol) in dichloromethane (7 ml) at 0° C. The reaction mixture was stirred for 1.5 hours at ambient temperature. The reaction mixture was washed with 1M NaOH (20 ml), 1M HCl (20 ml) brine (20 ml) and then dried over Na$_2$SO$_4$. After removal of the solvent the residue was purified by flash chromatography over silica gel (eluant: hexane/ethyl acetate 7:3).

0.75 g (45.7% of theory) of 3-difluoromethyl-1-methyl-1H-pyrazole-4-carboxylic acid [2-(2,4-dichlorophenyl)-1-methyl-ethyl]-ethoxy-amide (compound 1.031) was obtained in form of a white solid (m.p. 116-118° C.).

$^1$H NMR: (CDCl$_3$, 400 MHz):
1.14-1.20 (t, 3H); 1.36-1.45 (2d, 3H); 2.98-3.03 (dd, 1H); 3.19-3.25 (dd, 1H); 3.74-3.82 (q, 3H); 3.94 (s, 3H); 4.64-4.70 (m, 1H); 6.93-7.65 (m, 5H).

MS [M+H]$^+$ 406/408/410.

Example P7

Preparation of 3-difluoromethyl-1-methyl-1H-pyrazole-4-carboxylic acid ethoxy-[1-methyl-2-(2,4,6-trichlorophenyl)-ethyl]-amide (compound 1.032)

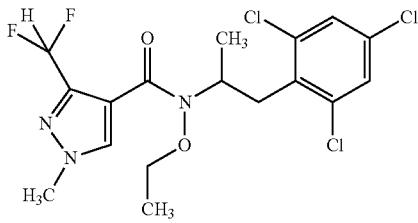

To a solution of O-ethyl-N-[1-methyl-2-(2,4,6-trichlorophenyl)-ethyl]-hydroxylamine (0.5 g, 1.63 mmoles) in dichloromethane (5 ml) was added triethylamine (0.566 ml, 4.07 mmloes) followed by drop wise addition of a solution 3-difluoromethyl-1-methyl-1H-pyrazole-4-carbonyl chloride (0.34 g, 1.79 mmol) in dichloromethane at a temperature of 0° C. After the complete addition of acid chloride the mixture was stirred for 18 hours at ambient temperature. When the TLC confirmed completion of the reaction, the reaction mass was diluted with water and extracted with dichloromethane (3×60 ml). The combined dichloromethane layer were washed with 2N HCl, followed by saturated NaHCO$_3$, then water and finally brine, dried over sodium sulfate and evaporated off solvent under reduced pressure. Resulting crude mass was purified by column chromatography using 60-120µ mesh silica gel and product collected at 30% ethyl acetate in hexane as eluent to give 3-difluoromethyl-1-methyl-1H-pyrazole-4-carboxylic acid ethoxy-[1-methyl-2-(2,4,6-trichloro-phenyl)-ethyl]-amide (0.390 g, 50%) as off white solid. m.p: 111-114° C.

$^1$H NMR (400 MHz, CDCl$_3$): δ 1.20-1.24 (t, 3H), 1.35-1.37 (d, 3H), 3.23-3.28 (dd, 1H), 3.33-3.38 (dd, 1H), 3.84-3.88 (q, 2H), 3.96 (s, 3H), 4.86-4.91 (m, 1H), 7.01-7.25 (t, 1H), 7.28 (s, 2H), 7.83 (s, 1H)

MS [M+H]$^+$ 439.9/441.83

Example P8

Preparation of 3-difluoromethyl-1-methyl-1H-pyrazole-4-carboxylic acid [2-(2,4-dichlorophenyl)-1-methyl-ethyl]-isopropoxy-amide (compound 1.033)

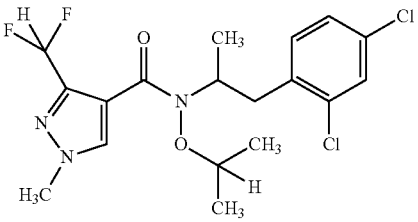

A solution of 3-difluoromethyl-1-methyl-1H-pyrazole-4-carbonyl chloride (1.1 g; 5.7 mmol) in dichloromethane (5 ml) was added dropwise to a stirred solution of N-[2-(2,4-dichlorophenyl)-1-methyl-ethyl]-O-isopropyl-hydroxylamine (1.5 g; 5.7 mmol), prepared as described in example P20, triethylamine (1.6 ml; 11.4 mmol) in dichloromethane (10 ml) at 0° C. The reaction mixture was stirred over night at ambient temperature. After removal of the solvent the residue was purified by flash chromatography over silica gel (eluant: c-hexane/ethyl acetate 7:3).

1.30 g (54.0% of theory) of 3-difluoromethyl-1-methyl-1H-pyrazole-4-carboxylic acid [2-(2,4-dichlorophenyl)-1-methyl-ethyl]-isopropoxy-amide (compound 1.033) was obtained in form of a yellow oil.

$^1$H NMR: (CDCl$_3$, 400 MHz):
0.91-0.93+1.11-1.13 (2d, 6H); 1.42-1.48 (2d, 3H); 3.00-3.07 (dd, 1H); 3.29-3.36 (dd, 1H); 3.92 (s, 3H); 3.97-4.36 (m, 1H); 4.36-4.45 (m, 1H); 6.97-7.59 (m, 5H).

MS [M+H]$^+$ 420/422/424.

Example P9

Preparation of 3-difluoromethyl-1-methyl-1H-pyrazole-4-carboxylic acid [2-(2,4-dichlorophenyl)-pentyl]-methoxy-amide (compound 1.059)

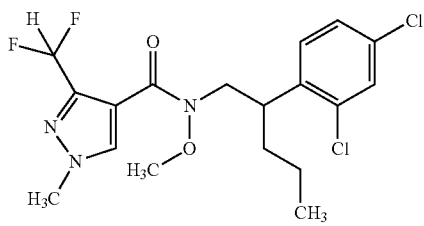

A solution of 3-difluoromethyl-1-methyl-1H-pyrazole-4-carbonyl chloride (2.20 g; 11.0 mmol) in dichloromethane (10 ml) was added dropwise to a stirred solution of N-[2-(2,4-dichlorophenyl)-pentyl]-O-methyl-hydroxylamine (3.0 g; 11.0 mmol), prepared as described in example P22, triethylamine (3.0 ml; 22 mmol) in dichloromethane (20 ml) at 0° C. The reaction mixture was stirred for 6 hours at ambient temperature. After removal of the solvent the residue was purified by flash chromatography over silica gel (eluant: c-hexane/ethyl acetate 1:1).

3.85 gm (83% of theory) of 3-difluoromethyl-1-methyl-1H-pyrazole-4-carboxylic acid [2-(2,4-dichlorophenyl)-pentyl]-methoxy-amide (compound 1.059) was obtained in form of a yellow oil.

$^1$H NMR: (CDCl$_3$, 400 MHz):

0.84-0.87 (t, 3H); 1.14-1.25 (m, 2H); 1.61-1.69 (m, 2H); 3.55 (s, 3H); 3.71-3.80 (m, 1H); 3.80-3.84 (dd, 1H); 3.96 (s, 3H); 3.99-4.05 (dd, 1H); 7.07-7.36 (m, 4H); 7.79 (s, 1H).

MS [M+H]$^+$ 420/422/424.

Example P10

Preparation of 3-difluoromethyl-1-methyl-1H-pyrazole-4-carboxylic acid methoxy-1'-methyl-3-(2,4,6-trichloro-phenyl)-propyls-amide (compound 2.003)

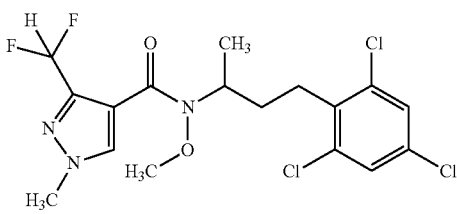

To a solution of O-Methyl-N-[1-methyl-3-(2,4,6-trichloro-phenyl)-propyl]-hydroxylamine (0.6 g, 2.1 mmol) prepared as described in example P23d, in dichloromethane (6 ml), was added triethylamine (0.73 ml, 5.2 mmol) followed by drop wise addition of a solution of 3-difluoromethyl-1-methyl-1H-pyrazole-4-carbonyl chloride (0.415 g, 2.1 mmol) in dichloromethane at 0° C. After complete addition of acid chloride, the reaction mixture was stirred for 18 hours at ambient temperature. When the TLC confirmed completion of the reaction, the reaction mass was diluted with water and extracted with dichloromethane (3×60 ml). The combined dichloromethane layer was washed with 2N HCl, followed by sat NaHCO$_3$ then water and finally brine solution, dried over sodium sulfate and solvent was evaporated off under reduced pressure. The resulting crude mass was purified by column chromatography using 60-120µ mesh silica gel and product collected at 30% ethyl acetate in hexane as eluent to give 3-difluoromethyl-1-methyl-1H-pyrazole-4-carboxylic acid methoxy-[1-methyl-3-(2,4,6-trichloro-phenyl)-propyl]amide (0.53 g, 57%) as a gum like mass.

Physical Data:

$^1$H NMR: (CDCl$_3$, 400 MHz):

1.41 (d, 3H, CH$_3$), 1.71-1.80 (m, 1H, CH$_2$), 1.94-2.04 (m, 1H, CH$_2$), 1.87-1.92 (m, 2H, CH$_2$), 3.78 (s, 3H, CH$_3$), 3.98 (s, 3H, CH$_3$), 4.66-4.71 (m, 1H, CH), 7.11 (t, 1H, CHF$_2$), 7.28 (s, 2H, Ar—H), 7.88 (s, 1H, pyrazole-H)

MS [M+H]$^+$ 440/442/444/446.

Example P11

Preparation of 3-difluoromethyl-1-methyl-1H-pyrazole-4-carboxylic acid methoxy-[3-(2,4,6-trichloro-phenyl)-propyl]-amide (compound 2.040)

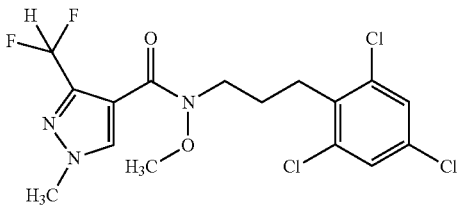

To a stirred solution of O-methyl-N-[3-(2,4,6-trichloro-phenyl)-propyl]-hydroxylamine (0.35 g, 1.3 mmol) prepared as described in example P24c in dichloromethane (5 ml), triethylamine (0.55 ml, 3.9 mmol) and a solution of 3-difluoromethyl-1-methyl-1H-pyrazole-4-carbonyl chloride acid in dichloromethane (2 ml) was added slowly at a temperature of 0° C. After complete addition of the acid chloride the mixture was stirred at ambient temperature for the next 3 hours. When the TLC confirmed the completion of the reaction, the reaction mass was diluted with water and extracted with dichloromethane (3×60 ml). The combined dichloromethane layer was washed with 2N HCl followed by saturated NaHCO$_3$ solution, water and finally brine. The organic layer was then dried over anhydrous sodium sulphate and concentrated under reduced pressure. The resulting crude mass was purified over column chromatography (silica gel 60-120 mesh, 26% ethylacetate in hexane) to afford 3-Difluoromethyl-1-methyl-1H-pyrazole-4-carboxylic acid methoxy-[3-(2,4,6-trichloro-phenyl)-propyl]-amide (0.5 g, 91%) as white crystalline solid. m.p-95-96° C.

Physical Data:

$^1$H NMR: (CDCl$_3$, 400 MHz):

1.89-1.96 (m, 2H, CH$_2$), 2.91-2.95 (m, 2H, CH$_2$), 3.66 (s, 3H, CH$_3$), 3.83-3.86 (t, 2H, CH$_2$), 3.97 (s, 3H, CH$_3$), 7.31 (t, 1H, CHF$_2$), 7.28 (s, 2H, Ar—H), 7.89 (s, 1H, pyrazole-H)

MS [M+H]$^+$ 426/428/430/432

Example P12

Preparation of 3-difluoromethyl-1-methyl-1H-pyrazole-4-carboxylic acid [3-(4-tert.-butyl-phenyl)-2-methyl-propyl]-methoxy-amide (compound 2.057)

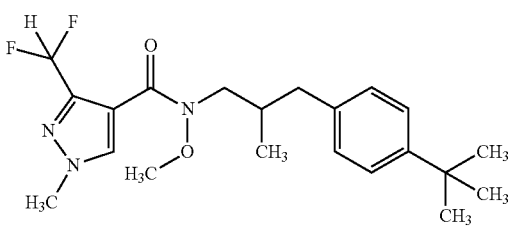

A solution of 3-difluoromethyl-1-methyl-1H-pyrazole-4-carbonyl chloride (0.89 g; 4.6 mmol) in dichloromethane (5 ml) was added dropwise to a stirred solution of N-[3-(4-tert-butyl-phenyl)-2-methyl-propyl]-O-methyl-hydroxylamine (1.0 g; 4.2 mmol), prepared as described in example P25, triethylamine (0.86 ml; 6.3 mmol) in dichloromethane (7 ml) at 0° C. The reaction mixture was stirred for 1.5 hours at ambient temperature. The reaction mixture was washed with 1M NaOH (20 ml), 1M HCl (20 ml) brine (20 ml) and then dried over $Na_2SO_4$. After removal of the solvent the residue was purified by flash chromatography over silica gel (eluant: hexane/ethyl acetate 7:3).

0.59 g (35.3% of theory) of 3-difluoromethyl-1-methyl-1H-pyrazole-4-carboxylic acid [3-(4-tert.-butyl-phenyl)-2-methyl-propyl]-methoxy-amide (compound 2.057) was obtained in form of a resin.

$^1$H NMR: ($CDCl_3$, 400 MHz):
0.90-0.95 (d, 3H); 1.30 (s, 9H); 2.24-2.36 (m, 1H); 2.39-2.45 (dd, 1H); 2.67-2.72 (dd, 1H); 3.58 (s, 3H); 3.68-3.70 (d, 2H); 3.98 (s, 3H); 7.09-7.11 (d, 2H); 7.15-7.42 (m, 3H); 7.90 (s, 1H).
MS $[M+H]^+$ 394.

Example P13

Preparation of N-[2-(4-chloro-phenyl)-1-methyl-ethyl]-O-methyl-hydroxylamine a) Preparation of 1-(4-chloro-phenyl)-propan-2-one O-methyl-oxime

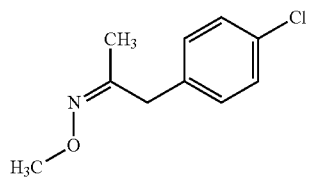

A solution of 1-(4-chloro-phenyl)-propan-2-one (8.5 g, 50.4 mmole) in methanol (100 ml) was treated with pyridine (5.2 ml, 62 mmol) followed by O-methyl hydroxylamine hydrochloride (5.20 g, 62 mmol). The resulting mixture was stirred at 23° C. over night for 16 hours. The reaction mixture was poured onto water (200 ml) and extracted with dichlorometane (3×50 ml). The organic layers were washed with brine and dried over anhydrous $Na_2SO_4$. After removal of the solvent the residue was purified by flash chromatography over silica gel (eluent: c-hexane/ethyl acetate 9:1).

7.38 g (74% of theory) of 1-(4-chloro-phenyl)-propan-2-one O-methyl-oxime was obtained in form of a clear liquid.
$^1$H NMR: ($CDCl_3$, 400 MHz):
1.71 (s, 3H); 3.48+3.52 (2s, 2H); 3.87-3.89 (2s, 3H); 7.13-7.22 (m, 4H).
MS $[M+H]^+$ 198/200.

b) Preparation of N-[2-(4-chloro-phenyl)-1-methyl-ethyl]-O-methyl-hydroxylamine

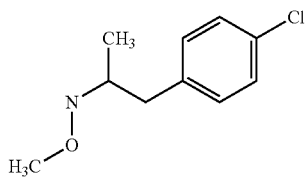

A solution of 1-(4-chloro-phenyl)-propan-2-one O-methyl-oxime (1.0 g, 5.1 mmol) in acetic acid (7.6 ml) was treated at 10° C. with sodium cyanoborohydride (641 mg, 10.2 mmol) added in small portions over 10 minutes and the resulting solution was stirred at 24° C. for 5 hours. The solvent was evaporated under reduced pressure (co-evaporation with toluene twice) and the residue was slurried with water and pH was adjusted to 9 with 1M NaOH. The aqueous phase was extracted with dichloromethane (2×20 ml), washed with brine and dried over anhydrous $Na_2SO_4$. After removal of the solvent (100 mbar; 45° C.), the residue (910 mg) was purified by flash chromatography over silica gel (eluent: c-hexane/ethyl acetate 9:1).

830 mg (82.0% of theory) of N-[2-(4-chloro-phenyl)-1-methyl-ethyl]-O-methyl-hydroxylamine was obtained in form of a clear liquid.
$^1$H NMR: ($CDCl_3$, 400 MHz):
1.02-1.06 (d, 3H); 2.54-2.59 (dd, 1H); 2.79-2.84 (dd, 1H); 3.14-3.24 (m, 1H), 3.52 (s, 3H); 5.3-5.5 ($s_{br}$, 1H); 7.12-7.16 (m, 2H); 7.25-7.28 (m, 2H).
MS $[M+H]^+$ 200/202.

Example P14

Preparation of N-[2-(2,4-dichlorophenyl)-1-methyl-ethyl]-O-methyl-hydroxylamine a) Preparation of 1-(2,4-dichlorophenyl)-propan-2-one O-methyl-oxime

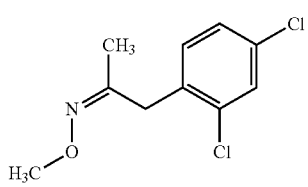

A solution of O-methyl hydroxylamine hydrochloride (7.04 g, 0.0843 mol) in a mixture of water (130 ml) and THF (50 ml) was treated with sodium acetate (5.9 g, 0.0720 mol) followed by 1-(2,4-dichlorophenyl)-propan-2-one (10 g, 0.0496 mole) and the resulting mixture was stirred at 23° C. for 4 hours. The reaction mixture was then diluted with ethylacetate, washed with brine and dried over anhydrous $Na_2SO_4$. The solvent was evaporated under reduced pressure (100 mbar; 45° C.).

13.5 g (100% of theory) of crude 1-(2,4-dichlorophenyl)-propan-2-one O-methyl-oxime was obtained in form of a clear liquid which was used without further purification for the next step.

$^1$H NMR: (CDCl$_3$, 400 MHz):

1.76 (s, 3H); 3.60+3.78 (2s, 2H); 3.87 (s, 3H); 7.12-7.19 (m, 2H); 7.39 (d, 1H).

MS [M+H]$^+$ 232/234/236.

b) Preparation of N-[2-(2,4-dichlorophenyl)-1-methyl-ethyl]-O-methyl-hydroxylamine

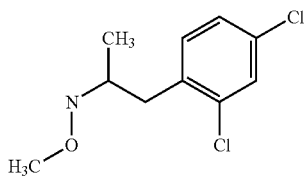

A solution of 1-(2,4-dichlorophenyl)-propan-2-one O-methyl-oxime (10.0 g, 0.0431 mol) in acetic acid (100 ml) was treated at 10° C. with sodium cyanoborohydride (5.41 g, 0.0862 mol) added in small portions over 15 minutes and the resulting solution was stirred at 24° C. for 6 hours. The solvent was evaporated under reduced pressure (co-evaporation with toluene twice) and the residue was slurried with water and pH was adjusted to 9 with 2M NaOH. The aqueous phase was extracted with dichloromethane (2×100 ml), washed with brine and dried over anhydrous Na$_2$SO$_4$. The solvent was evaporated under reduced pressure (100 mbar; 45° C.).

8.13 g (81.3% of theory) of crude N-[2-(2,4-dichlorophenyl)-1-methyl-ethyl]-O-methyl-hydroxylamine was obtained in form of a clear liquid which was used without further purification for the next step.

$^1$H NMR: (CDCl$_3$, 400 MHz):

1.04-1.09 (d, 3H); 2.66-2.71 (dd, 1H); 2.93-2.99 (dd, 1H); 3.25-3.33 (m, 1H), 3.52 (s, 3H); 5.2-5.4 (s$_{br}$, 1H); 7.17-7.18 (m, 2H); 7.35 (d, 1H).

MS [M+H]$^+$ 234/236/238.

Example P15

Preparation of O-methyl-N-[1-methyl-2-(2,4,6-trichlorophenyl)-ethyl]-hydroxylamine a) Preparation of 1,3,5-trichloro-2-((E)-2-nitro-propenyl)-benzene

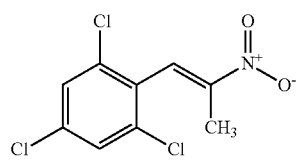

To a stirred solution of 2,4,6-trichloro-benzaldehyde (19 g, 90.69 mmol) and ammonium acetate (16.75 g, 217 mmol) in acetic acid (76 ml, 4 Vol.), nitroethane (45.1 ml, 625 mmol) was added in drops at a temperature of 0° C. The reaction mass was stirred at a temperature of 100° C. for 90 minutes. When the TLC confirmed the completion of the reaction, the reaction mass was allowed to attain ambient temperature and was diluted with ice cold water (700 ml), further aqueous layer was then extracted with ethyl acetate (3×50 ml). Combined ethyl acetate layer was washed with saturated sodium bicarbonate solution to neutral pH, then with water, followed by brine wash and dried under anhydrous Na$_2$SO$_4$ before the complete evaporation of solvents. The resulting crude mass was purified by column chromatography using 60-120µ mesh silica gel and product collected at 1% ethyl acetate in hexane as elution system to give 1,3,5-trichloro-2-((E)-2-nitro-propenyl)-benzene (15 g, 61%)

$^1$H NMR (400 MHz, CDCl$_3$): δ 2.10 (s, 3H, CH$_3$), 7.24 (s, 2H, Ar—H), 7.77 (s, 1H, CH)

b) Preparation of 1-(2,4,6-trichloro-phenyl)-propan-2-one

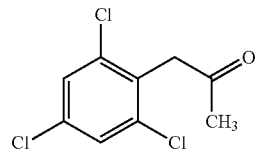

To a stirred solution of above obtained nitrostyrene (5 g, 18.72 mmol) in water (20 ml) and methanol (60 ml), was added Iron powder (2.355 gms, 42.12 mmol) followed by conc. HCl (11.5 ml, 112 mmol) at ambient under nitrogen atmosphere. The reaction mixture was stirred at 70° C. for 1 hour. After 1 hour, the remaining quantity of iron powder (2.355 gms, 42.12 mmol) and conc. HCl (11.5 ml, 112 mmol) was added to this reaction mass and stirring continued for 2 hours at 70° C. When TLC confirmed the completion of the reaction, reaction mass was cooled to ambient temperature and methanol was removed with a rotavapor. The resulting residue was then diluted with water and extracted with ethyl acetate (3×80 ml). The combined ethyl acetate layer was finally washed with water, followed by brine wash and dried under anhydrous sodium sulfate before the complete evaporation of solvents. The resulting crude mass was purified by column chromatography using 60-120µ mesh silica gel and product collected at 5% ethyl acetate in hexane as elution system to give 1-(2,4,6-trichloro-phenyl)-propan-2-one (3.7 g, 83.3%).

$^1$H NMR (400 MHz, CDCl$_3$): δ 2.26 (s, 3H, CH$_3$), 4.05 (s, 2H, CH$_2$), 7.34 (s, 2H, Ar—H)

c) Preparation of 1-(2,4,6-trichlorophenyl)-propan-2-one O-methyl-oxime

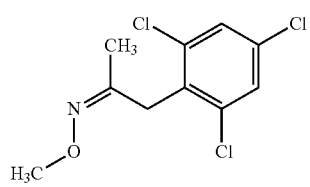

A solution of O-methyl-hydroxylamine hydrochloride (0.79 g, 9.4 mmol) in methanol (20 ml) was treated with triethylamine (1.32 ml, 9.4 mmol) followed by 1-(2,4,6-trichlorophenyl)-propan-2-one (1.5 g, 6.31 mmole). The resulting mixture was stirred at 60° C. for 3 hours. The reaction mixture was quenched with water and methanol was evaporated off. The resulting aqueous medium was extracted with ethylacetate (3×50 ml). The combined organic layers were washed with brine and dried over anhydrous Na$_2$SO$_4$. The solvent was evaporated under reduced pressure (100 mbar; 45° C.). The resulting crude mass was purified by column chromatography using 60-120µ mesh silica gel and product collected at 2% ethyl acetate in hexane as elution system to give 1-(2,4,6-Trichloro-phenyl)-propan-2-one O-methyl-oxime (1.2 g, 76%), which was taken up for further reduction.

d) Preparation of O-methyl-N-[1-methyl-2-(2,4,6-trichlorophenyl)-ethyl]-hydroxylamine

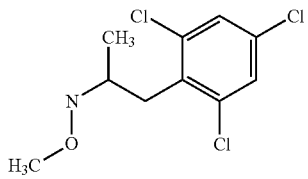

To a stirred solution of the above obtained 1-(2,4,6-trichloro-phenyl)-propan-2-one O-methyl-oxime (1.2 g, 4.51 mmol) in 12 ml of acetic acid, sodiumcyanoborohydride (0.568, 9 mmol) was added. The reaction mass was stirred at ambient temperature for 6 hours. When the TLC confirmed the completion of reaction, the solvent was evaporated under reduced pressure (co-evaporation with toluene twice). The resulting residue was diluted with water and the pH was adjusted to 9 with 2 N sodium hydroxide solution, which was then extracted with ethyl acetate (3×50 ml). The combined organic layer was washed with brine followed by drying over anhydrous sodium sulfate before evaporating the solvent. The resulting crude mass was purified by column chromatography using 60-120µ mesh silica gel and the product collected at 5% ethyl acetate in hexane as elution system to afford O-Methyl-N-[1-methyl-2-(2,4,6-trichloro-phenyl)-ethyl]-hydroxylamine (0.91 g, 75%).

$^1$H NMR (400 MHz, CDCl$_3$): δ 0.91-0.93 (d, 3H), 2.72-2.77 (dd, 1H), 2.98-3.03 (dd, 1H), 3.25-3.30 (m, 1H), 3.93 (s, 3H), 7.15 (s, 2H)

Example P16

Preparation of N-{2-[4-(4-chloro-phenoxy)-phenyl]-1-methyl-ethyl}-O-methyl-hydroxylamine a) Preparation of 1-[4-(4-chlorophenoxy)-phenyl]-propan-2-one O-methyl-oxime

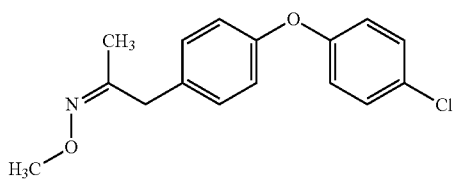

A solution of 1-[4-(4-chloro-phenoxy)-phenyl]-propan-2-one (10.0 g, 38 mmole) in methanol (65 ml) was treated with O-methyl hydroxylamine hydrochloride (3.90 g, 47 mmol) followed by pyridine (4.0 ml, 47 mmol). The resulting mixture was stirred at ambient temperature over night. The reaction mixture was poured onto water (150 ml) and extracted with dichloromethane (3×50 ml). The organic layers were washed with brine and dried over anhydrous Na$_2$SO$_4$.

11.0 g (100% of theory) of crude 1-[4-(4-chloro-phenoxy)-phenyl]-propan-2-one O-methyl-oxime was obtained in form of a yellow liquid which was used without further purification for the next step.

$^1$H NMR: (CDCl$_3$, 400 MHz):
1.73+1.81 (2s, 3H); 3.44+3.65 (2s, 2H); 3.88+3.89 (2s, 3H); 6.89-6.94 (m, 4H); 7.15-7.28 (m, 4H).
MS [M+H]$^+$ 290/292.

b) Preparation of N-{2-[4-(4-chloro-phenoxy)-phenyl]-1-methyl-ethyl}-O-methyl-hydroxylamine

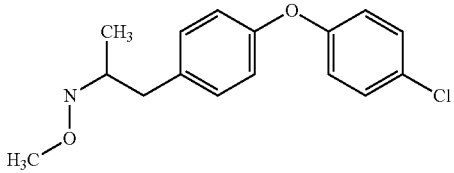

A solution of crude 1-[4-(4-chlorophenoxy)-phenyl]-propan-2-one O-methyl-oxime (6.0 g, 20.7 mmol) in acetic acid (50 ml) was treated at 10° C. with sodium cyanoborohydride (2.6 g, 41.4 mmol) added in small portions over 10 minutes and the resulting solution was stirred at 23° C. for 3.5 hours. The solvent was evaporated under reduced pressure (co-evaporation with toluene twice) and the residue was slurried with water and pH was adjusted to 11 with 1M NaOH. The aqueous phase was extracted with dichloromethane (2×20 ml), washed with brine and dried over anhydrous Na$_2$SO$_4$. After removal of the solvent (100 mbar; 45° C.), the residue (7.17 g) was purified by flash chromatography over silica gel (eluent: c-hexane). 3.91 g (65.0% of theory) of N-{2-[4-(4-chloro-phenoxy)-phenyl]-1-methyl-ethyl}-O-methyl-hydroxylamine was obtained in form of a clear liquid.

$^1$H NMR: (CDCl$_3$, 400 MHz):
1.07-1.09 (d, 3H); 2.53-2.62 (dd, 1H); 2.72-2.81 (dd, 1H); 3.16-3.26 (m, 1H), 3.54 (s, 3H); 5.3-5.5 (s$_{br}$, 1H); 6.86-6.94 (m, 4H); 7.14-7.18 (m, 2H); 7.24-7.29 (m, 2H).
MS [M+H]$^+$ 292/294.

Example P17

Preparation of N-[2-(2,4-dichlorophenyl)-1-methyl-ethyl]-hydroxylamine a) Preparation of 1-(2,4-dichlorophenyl)-propan-2-one oxime

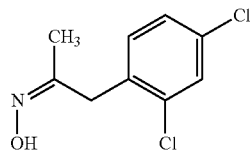

A solution of 1-(2,4-dichlorophenyl)-propan-2-one (3.46 g, 16.7 mmole) in methanol (40 ml) was treated with hydroxylamine hydrochloride (1.40 g, 20.6 mmol) followed by pyridine (1.7 ml, 20.6 mmol). The resulting mixture was stirred at ambient temperature over night for 16 hours. The reaction mixture was poured onto water (200 ml). The solid product was collected by filtration, washed with water and dried (40° C., 100 mbar). 3.63 g (100% of theory) of 1-(2,4-dichlorophenyl)-propan-2-one oxime was obtained in form of a white solid (m.p. 120-124° C.).

¹H NMR: (CDCl₃, 400 MHz):
1.86 (s, 3H); 3.61 (s, 2H); 7.12-7.21 (m, 2H); 7.39-7.41 (d, 1H); 8.2 ($s_{br}$, 1H).
MS [M+H]⁺ 218/220/222.

b) Preparation of N-[2-(2,4-dichlorophenyl)-1-methyl-ethyl]-hydroxylamine

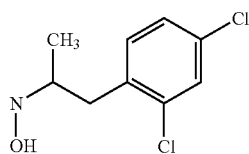

A solution of 1-(2,4-dichlorophenyl)-propan-2-one oxime (3.3 g, 15.1 mmol) in acetic acid (30 ml) was treated at 10° C. with sodium cyanoborohydride (1.90 g, 30.3 mmol) added in small portions over 10 minutes and the resulting solution was stirred at 23° C. for 5 hours. The solvent was evaporated under reduced pressure (co-evaporation with toluene twice) and the residue was slurried with water and pH was adjusted to 10 with 1M NaOH. The aqueous phase was extracted with dichloromethane (3×20 ml), washed with brine and dried over anhydrous Na₂SO₄. After removal of the solvent (100 mbar; 45° C.), 3.18 g (96.0% of theory) of N-[2-(2,4-dichlorophenyl)-1-methyl-ethyl]-hydroxylamine was obtained in form of a white solid (m.p. 83-86° C.).

¹H NMR: (CDCl₃, 400 MHz):
1.08-1.11 (d, 3H); 2.69-2.74 (dd, 1H); 2.98-3.03 (dd, 1H); 3.24-3.32 (m, 1H); 5.3-5.6 ($s_{br}$, 1H); 7.18-7.19 (m, 2H); 7.39 (m, 1H); 7.5-8.2 ($s_{br}$, 1H).
MS [M+H]⁺ 220/222/224.

Example P18

Preparation of N-[2-(2,4-dichlorophenyl)-1-methyl-ethyl]-O-ethyl-hydroxylamine a) Preparation of 1-(2,4-dichlorophenyl)-propan-2-one O-ethyl-oxime

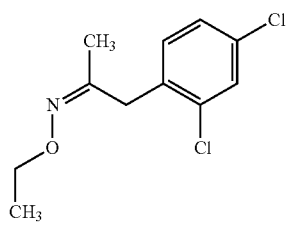

A solution of O-ethyl hydroxylamine hydrochloride (4.10 g, 42.1 mmol) in a mixture of water (130 ml) and THF (50 ml) was treated with sodium acetate (2.95 g, 72 mmol) followed by 1-(2,4-dichlorophenyl)-propan-2-one (5 g, 24.8 mmole) and the resulting mixture was stirred at 23° C. for 4 hours. The reaction mixture was then diluted with ethylacetate, washed with brine and dried over anhydrous Na₂SO₄. The solvent was evaporated under reduced pressure (90 mbar; 45° C.).

6.0 g (99% of theory) of crude 1-(2,4-dichlorophenyl)-propan-2-one O-ethyl-oxime was obtained in form of a clear liquid as an E/Z-mixture which was used without further purification for the next step.

¹H NMR: (CDCl₃, 400 MHz):
1.23-1.28 (2t, 3H); 1.74+1.76 (2s, 3H); 3.60+3.78 (2s, 3H); 4.09-4.16 (2q, 2H); 7.12-7.19 (m, 2H); 7.38 (d, 1H).
MS [M+H]⁺ 246/248/250.

b) Preparation of N-[2-(2,4-dichlorophenyl)-1-methyl-ethyl]-O-ethyl-hydroxylamine

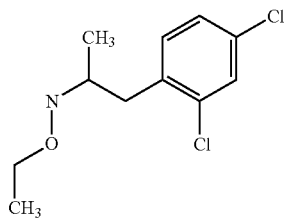

A solution of 1-(2,4-dichlorophenyl)-propan-2-one O-methyl-oxime (10.0 g, 0.0406 mol) in acetic acid (100 ml) was treated at 10° C. with sodium cyanoborohydride (5.41 g, 0.0862 mol) added in small portions over 10 minutes and the resulting solution was stirred at 24° C. for 6 hours. The solvent was evaporated under reduced pressure (co-evaporation with toluene twice) and the residue was slurried with water and pH was adjusted to 9 with 2M NaOH. The aqueous phase was extracted with dichloromethane (2×100 ml), washed with brine and dried over anhydrous Na₂SO₄. The solvent was evaporated under reduced pressure (100 mbar; 45° C.).

5.09 g (51.0% of theory) of crude N-[2-(2,4-dichlorophenyl)-1-methyl-ethyl]-O-ethyl-hydroxylamine was obtained in form of a clear liquid which was used without further purification for the next step.

¹H NMR: (CDCl₃, 400 MHz):
0.98-1.02+1.08-1.12 (2d, 3H); 1.13-1.18 (2t, 3H); 2.63-2.68+2.70-2.78 (2dd, 1H); 2.94-3.10+3.15-3.21 (m, 1H); 3.25-3.31+3.71-3.78 (2q, 2H); 5.0-5.5 ($s_{br}$, 1H); 7.16-7.19 (m, 2H); 7.34-7.36 (m, 1H).
MS [M+H]⁺ 248/250/252.

Example P20

Preparation of N-[2-(2,4-dichlorophenyl)-1-methyl-ethyl]-O-isopropyl-hydroxylamine a) Preparation of 1-(2,4-dichlorophenyl)-propan-2-one O-isopropyl-oxime

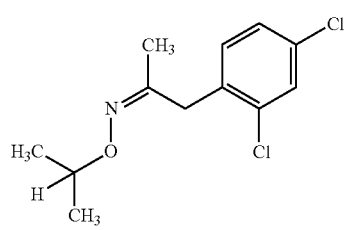

A solution of 1-(2,4-dichlorophenyl)-propan-2-one (5.1 g, 25.0 mmole) in methanol (45 ml) was treated with O-isopropyl-hydroxylamine hydrochloride (3.50 g, 31 mmol) followed by pyridine (2.6 ml, 31 mmole) and the resulting mixture was stirred at 23° C. over night. The reaction mixture was poured onto water (100 ml) and extracted with dichloromethane (3×50 ml). Organic layers were washed with brine and dried over anhydrous Na$_2$SO$_4$. The solvent was evaporated under reduced pressure (90 mbar; 45° C.).

6.48 g (99% of theory) of crude 1-(2,4-dichlorophenyl)-propan-2-one O-isopropyl-oxime was obtained in form of a clear liquid as an E/Z-mixture which was used without further purification for the next step.

$^1$H NMR: (CDCl$_3$, 400 MHz):
1.23-1.26 (d, 6H); 1.74 (s, 3H); 3.60+3.78 (2s, 3H); 4.25-4.38 (2m, 1H); 7.14-7.21 (m, 2H); 7.39 (d, 1H).
MS [M+H]$^+$ 260/262/264.

b) Preparation of N-[2-(2,4-dichlorophenyl)-1-methyl-ethyl]-O-isopropyl-hydroxylamine

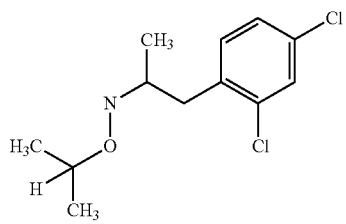

A solution of 1-(2,4-dichlorophenyl)-propan-2-one O-isopropyl-oxime (6.0 g, 23 mmol) in acetic acid (40 ml) was treated at 10° C. with sodium cyanoborohydride (2.90 g, 46 mmol) added in small portions over 15 minutes and the resulting solution was stirred at 24° C. for 4 hours. The solvent was evaporated under reduced pressure (co-evaporation with toluene twice) and the residue was slurried with water and pH was adjusted to 10 with 1M NaOH. The aqueous phase was extracted with dichloromethane (2×80 ml), washed with brine and dried over anhydrous Na$_2$SO$_4$. The solvent was evaporated under reduced pressure (100 mbar; 45° C.).

5.90 g (98.0% of theory) of crude N-[2-(2,4-dichlorophenyl)-1-methyl-ethyl]-O-isopropyl-hydroxylamine was obtained in form of a clear liquid which was used without further purification for the next step.

$^1$H NMR: (CDCl$_3$, 400 MHz):
1.03-1.07 (d, 3H); 1.13-1.19 (m, 6H); 2.61-2.68+2.94-3.03 (2dd, 2H); 3.21-3.31 (m, 1H); 3.78-3.84 (m, 1H); 5.2 (s$_{br}$, 1H); 7.14-7.18 (m, 2H); 7.35-7.36 (m, 1H).
MS [M+H]$^+$ 262/264/266.

Example P21

Preparation of O-Methyl-N-[2-(2,4,6-trichloro-phenyl)-ethyl]-hydroxylamine a) Preparation of 1,3,5-trichloro-2-chloromethyl-benzene

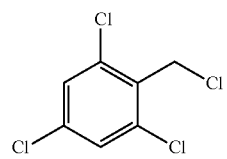

To a stirred solution of 2,4,6-trichlorobenzylalcohol (10.0 g; 47.3 mmoles) in chloroform (100 ml) kept under nitrogen atmosphere, thionyl chloride (6.07 mL, 85.1 mmoles) was added slowly at 0° C. over a period of 15 minutes followed by catalytic amount of DMF. The reaction mix was allowed to stir at ambient temp for 3 hours. The reaction mixture was quenched with 50 mL of water; the aqueous layer was extracted with DCM (3×100 ml). The combined organic layer was washed with 5% sodium bicarbonate solution (2×50 ml) followed by brine (50 ml) and dried over anhydrous sodium sulphate. The solvent was evaporated under reduced pressure. 10.9 g (100.0% of theory) of 1,3,5-trichloro-2-chloromethyl-benzene was obtained in form of a white solid.

1HNMR (CDCl$_3$, 400 MHz): δ=7.37 (2H, s); 4.82 (2H, s)
Mass: M=229.8 b) Preparation of (2,4,6-trichloro-phenyl)-acetonitrile

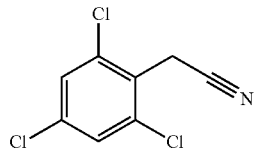

To a stirred solution of 1,3,5-trichloro-2-chloromethyl-benzene (12.85 g, 58.8 mmole) in ethanol (45 ml), NaCN (3.20, 67.0 mmole) solution in water (15 ml) was added at ambient temperature. The reaction mixture was refluxed for 4 hours to complete the reaction. Ethanol was evaporated and the reaction mixture was diluted with water (50 ml). The aqueous layer was extracted with EtOAc (3×100 ml). The combined organic layer was washed with brine (30 ml) and dried over sodium sulfate. Organic layer was concentrated under vacuum to give white solid. Crude product was purified by chromatography on silica-gel column to afford 9.0 g (75.0% of theory) of (2,4,6-trichloro-phenyl)-acetonitrile 1HNMR (CDCl$_3$, 400 MHz): 7.41 (s, 2H); 3.97 (s, 2H).
Mass: M=218.9 c) Preparation of (2,4,6-trichloro-phenyl)-acetaldehyde

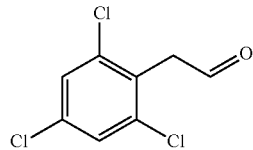

To the stirred, cold solution (−70° C.) of (2,4,6-trichloro-phenyl)-acetonitrile (5.7 g, 26.0 mmole) in toluene (120 ml) kept under N2 atmosphere, DIBAL-H (28.1 ml 1M solution in THF, 28.6 mmole) was added dropwise over a period of 30 min. Reaction was stirred for 3 hrs at −70° C. After completion of reaction, it was quenched by dropwise addition of HCl (60 ml, 2N) at
−40° C. and was kept for 30 min at ambient temperature. Toluene layer was separated and aq. layer was extracted with ethyl acetate (3×100 ml) and. The combined organic layer was washed with brine (30 ml) and dried over sodium sulfate. The organic layer was concentrated under vacuum. 4.5 g (78.0% of theory) of (2,4,6-trichloro-phenyl)-acetaldehyde was obtained in form of a white solid.

1HNMR (CDCl$_3$, 400 MHz: 9.70 (s, 1H); 7.38 (s, 2H); 4.08 (s, 2H)
Mass: M=246.9

Example P22

Preparation of N-[2-(2,4-dichlorophenyl)-pentyl]-O-methyl-hydroxylamine a) Preparation of 2-(2,4-dichlorophenyl)-pentanal O-methyl-oxime

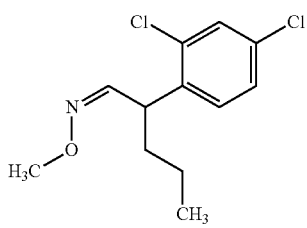

A solution of 2-(4-chloro-phenyl)-pentanal (10.0 g, 43.0 mmole) in methanol (75 ml) was treated with O-methyl hydroxylamine hydrochloride (4.40 g, 53 mmol) followed by pyridine (4.5 ml, 53 mmol). The resulting mixture was stirred at 23° C. over night. The reaction mixture was poured onto water (200 ml) and extracted with dichlorometane (3×50 ml). The organic layers were washed with brine and dried over anhydrous $Na_2SO_4$. The solvent was evaporated under reduced pressure (100 mbar; 45° C.).

11.20 g (100.0% of theory) of crude 2-(2,4-dichlorophenyl)-pentanal O-methyl-oxime was obtained in form of a clear liquid which was used without further purification for the next step.

MS $[M+H]^+$ 260/262/264.

b) Preparation of N-[2-(2,4-dichlorophenyl)-pentyl]-O-methyl-hydroxylamine

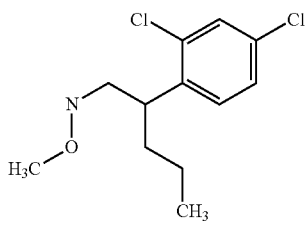

A solution of 2-(2,4-dichlorophenyl)-pentanal O-methyl-oxime (6.0 g, 23 mmol) in acetic acid (50 ml) was treated at 10° C. with sodium cyanoborohydride (2.90 g, 46 mmol) added in small portions over 10 minutes and the resulting solution was stirred at 24° C. for 4 hours. The solvent was evaporated under reduced pressure (co-evaporation with toluene twice) and the residue was slurried with water and pH was adjusted to 11 with 1M NaOH. The aqueous phase was extracted with dichloromethane (2×50 ml), washed with brine and dried over anhydrous $Na_2SO_4$. After removal of the solvent (100 mbar; 45° C.), the residue (6.2 g) was purified by flash chromatography over silica gel (250 g; eluent: c-hexane). 5.15 g (79.0% of theory) of N-[2-(2,4-dichlorophenyl)-pentyl]-O-methyl-hydroxylamine was obtained in form of a clear liquid.

$^1$H NMR: ($CDCl_3$, 400 MHz):

0.82-0.89 (t, 3H); 1.12-1.27 (m, 2H); 1.49-1.58 (m, 1H); 1.63-1.72 (m, 1H); 3.05-3.10 (dd, 1H); 3.12-3.18 (dd, 1H); 3.47 (s, 3H), 3.50-3.51 (m, 1H); 5.0-5.50 ($s_{br}$, 1H); 7.14-7.16 (m, 1H); 7.21-7.25 (m, 1H); 7.37-7.39 (m, 1H).

MS $[M+H]^+$ 262/264/266.

Example P23

Preparation of O-Methyl-N-[1-methyl-3-(2,4,6-trichloro-phenyl)-propyl]-hydroxylamine a) Preparation of 3-(2,4,6-trichloro-phenyl)-propionic acid

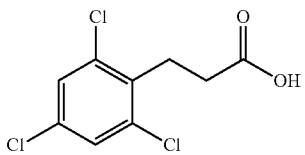

Meldrum's acid (2.06 g, 14.32 mmoles) was added to TEAF (7.05 ml) at ambient temperature under stirring and the reaction mixture was kept under nitrogen atmosphere. After 10 min 2,4,6-trichloro benzaldehyde (3 g, 14.32 mmoles) was added to the reaction mixture. It was then refluxed at 120° C. for 3 hrs. On completion of the reaction, the mixture was cooled at ambient and was poured into ice water (50 ml). Then aq. layer was extracted with ethyl acetate (3×80 ml), the combined organic layer was washed with brine (40 ml) and dried over sodium sulphate. Organic layer was concentrated under vacuum. 3.10 g (86.0% of theory) of 3-(2,4,6-trichloro-phenyl)-propionic acid was obtained in form of a white solid.

$^1$H NMR (400 MHz, $CDCl_3$):

7.32 (s, 2H); 3.26-3.22 (m, 2H); 2.63-2.58 (m, 2H).

MS $[M+H]^+$ 253/255/257

TEAF (triethyl ammonium formate) preparation: To formic acid (1.12 g~0.93 ml, 24.5 mmoles) solution kept under nitrogen was added slowly triethylamine (1 g~1.37 ml, 9.8 mmoles) at 0° C. and the mixture was stirred for one and half hour at ambient temperature.

b) Preparation of N-methoxy-N-methyl-3-(2,4,6-trichloro-phenyl)-propionamide

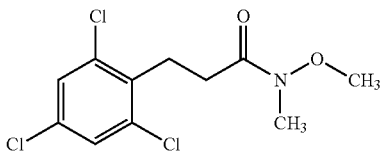

To a solution of acid chloride in chloroform [acid chloride was prepared from corresponding 3-(2,4,6-trichloro-phenyl)-propionic acid (5 g, 19.7 mmoles) using thionyl chloride (5.87 g, 49.4 mmole) under refluxing condition at 110° C. for 3 hours] N,O-dimethylhydroxylamine hydrochloride (2.3 g, 23.9 mmoles) followed by pyridine (3.77 ml, 47.7 mmole) was added drop wise at 0° C. The reaction mix was stirred at ambient temperature for 3 hours. On completion, the reaction mix was diluted with 70 ml DCM and 40 ml of water. Organic layer was separated and the aqueous layer was extracted two times with DCM (50 ml×2). The combined organic layer was washed with brine (40 ml) and dried over sodium sulfate. After removal of the solvent the residue was purified by chromatography over silica gel. 3.0 g (52.0% of theory) of N-methoxy-N-methyl-3-(2,4,6-trichloro-phenyl)-propionamide was obtained in form of a solid.

¹H NMR (CDCl₃, 400 MHz):
7.31 (s, 2H); 3.67 (s, 3H); 3.24-3.19 (m, 2H); 3.19 (s, 3H); 2.67-2.63 (m, 2H)
MS [M+H]⁺ 296/298/300 c) Preparation of
4-(2,4,6-trichloro-phenyl)-butan-2-one

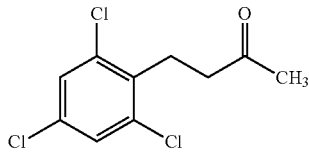

To the stirred and cold solution (0° C.) of N-methoxy-N-methyl-3-(2,4,6-trichloro-phenyl)-propionamide (1 g, 3.37 mmol) in THF (15 ml) kept under nitrogen atmosphere, MeMgI (1.3 mL of 3M ether solution, 3.9 mmole) was added and stirring was continued at 0° C. for 2 hours. Reaction mixture was quenched with 5% of HCl (10 ml) at 0° C. and aqueous layer was extracted with EtOAc (3×30 ml). The combined organic layer was washed with 20 ml of brine and dried over sodium sulfate; concentrated under vacuum to give off-white solid. The residue was purified by chromatography over silica gel. 0.50 g (60.0% of theory) of 4-(2,4,6-trichloro-phenyl)-butan-2-one was obtained in form of a solid.

¹H NMR (CDCl₃, 400 MHz):
2.14 (s, 3H, CH₃), 2.72-2.76 (t, 2H, CH₂), 2.93-2.97 (t, 2H, CH₂), 7.13-7.16+7.16-7.19 (2d, 2H, Ar—H), 7.34-7.35 (d, 1H, Ar—H).
MS [M+H]⁺ 252/254/256 d) Preparation of O-Methyl-N-[1-methyl-3-(2,4,6-trichloro-phenyl]-propyl-hydroxylamine

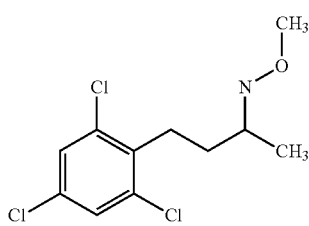

To a stirred solution of 4-(2,4,6-trichloro-phenyl)-butan-2-one (0.9 g, 3.57 mmol) in methanol (5 ml), was added triethylamine (0.73 ml, 5.3 mmol) and O-methyl-hydroxylamine hydrochloride (0.447 g, 5.3 mmol). The reaction mixture was heated at a temperature of 60° C. for 3 hours. When the TLC confirmed the completion of the reaction, the reaction mass was allowed to attain ambient temperature. After the reaction mixture was diluted with water and methanol was evaporated off, the aqueous layer was extracted with ethyl acetate (3×30 ml). The combined ethyl acetate layers were washed with water followed by brine solution and dried over sodium sulfate before complete evaporation of the solvents to give 4-(2, 4,6-trichloro-phenyl)-butan-2-one O-methyl-oxime (0.980 g) crude, which was taken up for reduction without any further purification.

To a solution of 4-(2,4,6-trichloro-phenyl)-butan-2-one O-methyl-oxime (0.650 g, 2.33 mmol) in acetic acid, sodiumcyanoborohydride (0.293 g, 4.66 mmol) was added. The reaction mass was stirred at room temp for 6 hours. When the TLC confirmed the completion of the reaction, the acetic acid in the reaction mass was removed by azeotropic distillation. The residue was then basified with 10% NaOH solution and it was extracted with ethyl acetate (3×30 ml). The combined ethyl acetate layers were washed with water followed by brine solution and dried over sodium sulfate before concentration. Resulting crude mass was purified by column chromatography using 60-120µ mesh silica gel and product collected at 3% ethyl acetate in hexane as eluent to give O-Methyl-N-[1-methyl-3-(2,4,6-trichloro-phenyl)-propyl]-hydroxylamine (0.6 g, 90%).

¹H NMR (400 MHz, CDCl₃): δ1.21 (d, 3H), 1.52-1.59 (m, 1H), 1.68-1.76 (m, 1H), 2.80-2.83 (q, 2H), 3.06-3.13 (m, 1H), 3.55 (s, 3H), 5.45 (s, 1H), 7.29 (s, 2H)

Physical Data:
¹H NMR (CDCl₃, 400 MHz):
1.21 (d, 3H, CH₃), 1.52-1.59 (m, 1H, CH₂), 1.68-1.76 (m, 1H, CH₂), 2.80-2.83 (m, 2H, CH₂), 3.06-3.13 (m, 1H, CH), 1.45 (s, 1H, NH), 7.29 (s, 2H, Ar—H)

Example P24

Preparation of O-Methyl-N-[3-(2,4,6-trichloro-phenyl)-propyl]-hydroxylamine a) Preparation of
3-(2,4,6-trichloro-phenyl)-propan-1-ol

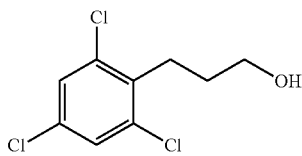

Physical Data:
¹H NMR (CDCl₃, 400 MHz):
1.79-1.86 (m, 2H, CH₂), 2.95-2.99 (m, 2H, CH₂), 3.71-3.749 (t, 2H, CH₂), 7.30 (s, 2H, Ar—H)

b) Preparation of
3-(2,4,6-trichloro-phenyl)-propionaldehyde

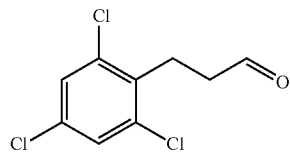

To a stirred solution N-methoxy-N-methyl-3-(2,4,6-trichloro-phenyl)-propionamide (0.9 g, 3.04 mmol) in toluene (18 mL), DIBAL-H (15.2 mL, 15.2 mmol) was added at −60° C. slowly in drops over a period of 20 minutes and the reaction mass was stirred at −60° C. for 3 hours. Reaction mass was then quenched with dil. HCl (20 ml) in drops, followed by dilution with water (10 ml) and stirred for 15 minutes. Toluene layer was separated and resulting aqueous phase was extracted with ethyl acetate (30 mL×3). The combined organic layer was washed with water and brine. The organic layer was then dried over anhydrous sodium sulphate and concentrated under reduced pressure. The resulting crude mass was purified over column chromatography (silica gel 60-120 mesh, 2% ethyl acetate in hexane) to afford white crystalline solid of 3-(2,4,6-trichloro-phenyl)-propionaldehyde (0.45 g, 62.5%)

¹H NMR (400 MHz, CDCl₃): δ 2.68 (t, 2H), 3.19-3.23 (t, 2H), 7.29 (s, 2H), 9.86 (s, 1H)

MS [M+H]⁺: 235.9/239.9

Physical Data:

¹H NMR (CDCl₃, 400 MHz):

2.68-2.72 (m, 2H, CH₂), 3.19-3.23 (m, 2H, CH₂), 7.29 (s, 2H, Ar—H), 9.86 (s, 1H, CHO)

c) Preparation of O-methyl-N-[3-(2,4,6-trichloro-phenyl)-propyl]-hydroxylamine

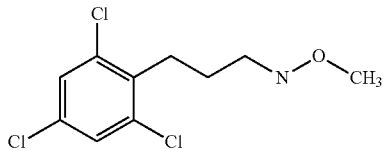

To a solution of 3-(2,4,6-trichloro-phenyl)-propionaldehyde (0.45 g, 1.8 mmol) in methanol (5 ml), triethylamine (0.4 ml, 2.8 mmol) followed by O-methylhydroxylamine-hydrochloride (0.24 g, 2.8 mmol) was added and the mixture was heated at 60° C. for 2 hours. When the TLC confirmed the completion of the reaction, the reaction mass was allowed to attain ambient temperature and quenched with water and methanol was removed with a rotavapor. The resulting aqueous solution was extracted with ethyl acetate (3×30 ml). The combined ethyl acetate layers were washed with water and dried over sodium sulfate before complete evaporation of the solvents to give the crude mass. The resulting crude mass was purified over column chromatography (silica gel 60-120 mesh, 1% ethyl acetate in hexane) to afford 3-(2,4,6-trichloro-phenyl)-propionaldehyde O-methyl-oxime (0.5 g, 80%)

To a stirred solution of 3-(2,4,6-trichloro-phenyl)-propionaldehyde O-methyl-oxime in acetic acid, NaCNBH₃ was added at 0° C.-10° C. The reaction mass was then stirred at ambient temperature for 6 hours. When the TLC confirmed completion of the reaction, acetic acid was removed by azeotropic distillation. The residue was basified with 10% NaOH solution and aqueous solution was extracted with ethyl acetate (3×30 ml). The combined organic layer was washed with water and brine. The organic layer was then dried over anhydrous sodium sulphate and concentrated under reduced pressure. The resulting crude mass was purified over column chromatography (silica gel 60-120 mesh, 3% ethyl acetate in hexane) to afford O-methyl-N-[3-(2,4,6-trichloro-phenyl)-propyl]-hydroxylamine (0.4 g, 88%).

¹H NMR (400 MHz, DMSO): δ 1.74-1.82 (m, 2H), 2.92-3.01 (m, 4H), 3.55 (s, 3H), 5.60 (s, 1H), 7.29 (s, 2H)

MS [M+H]⁺: 268.13/272.17

Physical Data:

¹H NMR (CDCl₃, 400 MHz):

1.74-1.82 (m, 2H, CH₂), 2.92-3.01 (m, 4H, CH₂—CH₂), 3.55 (s, 3H, CH₃), 5.60 (s, 1H, NH), 7.29 (s, 2H, Ar—H).

Example P25

Preparation of N-[3-(4-tert-butyl-phenyl)-2-methyl-propyl]-O-methyl-hydroxylamine a) Preparation of 3-(4-tert-butyl-phenyl)-methyl-propionaldehyde O-methyl-oxime

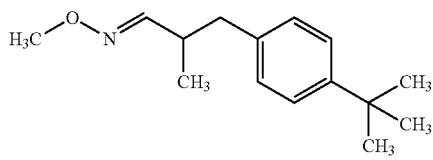

A solution of O-methyl hydroxylamine hydrochloride (3.30 g, 0.041 mol) in a mixture of water (65 ml) and THF (25 ml) was treated with sodium acetate (2.85 g, 0.0348 mol) followed by 3-(4-tert-butyl-phenyl)-methyl-propionaldehyde (5 g, 0.024 mole) and the resulting mixture was stirred at 23° C. for 4 hours. The reaction mixture was then diluted with ethylacetate, washed with brine and dried over anhydrous Na₂SO₄. The solvent was evaporated under reduced pressure (100 mbar; 45° C.).

6.01 g (100% of theory) of crude 3-(4-tert-butyl-phenyl)-methyl-propionaldehyde O-methyl-oxime was obtained in form of a clear liquid which was used without further purification for the next step.

MS [M+H]⁺ 234.

b) Preparation of N-[3-(4-tert-butyl-phenyl)-2-methyl-propyl]-O-methyl-hydroxylamine

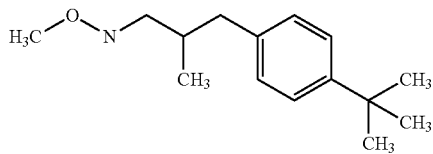

A solution of 3-(4-tert-butyl-phenyl)-methyl-propionaldehyde O-methyl-oxime (5.0 g, 0.0213 mol) in acetic acid (50 ml) was treated at 10° C. with sodium cyanoborohydride (2.63 g, 0.042 mol) added in small portions over 15 minutes and the resulting solution was stirred at 24° C. for 6 hours. The solvent was evaporated under reduced pressure (co-evaporation with toluene twice) and the residue was slurried with water and pH was adjusted to 9 with 2M NaOH. The aqueous phase was extracted with dichloromethane (2×100 ml), washed with brine and dried over anhydrous Na₂SO₄. The solvent was evaporated under reduced pressure (100 mbar; 45° C.).

4.52 g (89.5% of theory) of crude N-[3-(4-tert-butyl-phenyl)-2-methyl-propyl]-O-methyl-hydroxylamine was obtained in form of a clear liquid which was used without further purification for the next step.

MS [M+H]⁺236.

Example P26

Preparation of 2,4-dichloro-1-(1-methoxy-2-nitro-propyl)-benzene a) Preparation of 2,4-dichloro-1-((E)-2-nitro-propenyl)-benzene

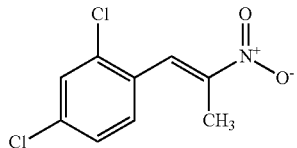

In a sulfonation flask 2,4-dichloro-benzaldehyde (77 g, 0.44 mol), nitroethane (216 ml, 3.04 mol) and ammonium acetate (81.4 g, 1.06 mol) were added to glacial acetic acid (600 ml). The resulting solution was heated to 90° C. for three hours. After removal of the solvent ice-water (400 ml) was added. The solid product was collected by filtration, washed with water and recrystallized from ethanol. 55.9 g (55% of theory) of 2,4-dichloro-1-((E)-2-nitro-propenyl)-benzene was obtained in the form of a yellow solid (m.p. 79-81° C.).

$^1$H NMR (400 MHz, CDCl$_3$): δ 8.11 (s, 1H), 7.51 (d, 1H), 7.34 (dd, 1H), 7.27 (d, 1H), 2.33 (s, 3H, CH$_3$).

b) Preparation of 2,4-dichloro-1-(1-methoxy-2-nitro-propyl)-benzene

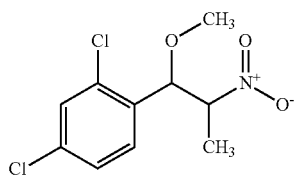

To a stirred yellow solution of the 2,4-dichloro-1-((E)-2-nitro-propenyl)-benzene (4 mmol, 0.93 g), in dry toluene (20 ml) under N$_2$ was added at 0° C. dropwise during 2 minutes a mixture of 5.4M CH$_3$ONa in methanol (16.2 mmol, 3 ml) and methanol (2 ml). After stirring for 1.5 h glacial acid (3 ml) was added, followed by water (20 ml). The aqueous solution was extracted with dichloromethane (2×30 ml), the organic layers were combined, dried (MgSO$_4$), filtered, and evaporated under reduced pressure to give 0.78 g crude 1-aryl-1-methoxy-2-nitropropanea yellow oil. This raw material was purified by column chromatography (silicagel, hexane/ethylacetate 8:2) to afford 0.45 g (43% of theory) of 2,4-dichloro-1-(1-methoxy-2-nitro-propyl)-benzene in the form of liquid, as a mixture of diastereomeres. $^1$H NMR (400 MHz, CDCl$_3$): δ 1.35-1.37+1.39-1.40 (2d, 3H, CH$_3$), 3.18+3.21 (2s, 3H, CH$_3$), 3.88+3.92 (2s, 3H, CH$_3$), 4.69-4.75 (m, 1H, CH), 5.16-5.18+5.39-5.40 (2d, 1H, CH), 7.15-7.47 (m, 3H, Ar—H).

MS [M+H]$^+$ 264/266/268.

Example P27

Preparation of 2,4-dichloro-1-(1-fluoro-2-nitro-propyl)-benzene a) Preparation of 1-(2,4-dichlorophenyl)-2-nitro-propan-1-ol

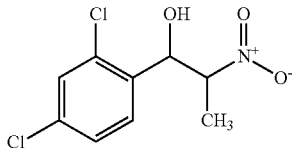

To a stirred solution of nitroethane (8.3 g, 0.11 mol) in acetonitrile (150 ml) was added anhydrous potassium phosphate (1.0 g, 4.6 mmol) followed by 2,4-dichloro-benzaldehyde (17.5 g, 0.10 mol). The reaction mixture was stirred for 4 hours. Water (300 ml) was added and the reaction mixture was extracted with diethyl ether (200 ml). The organic extract was washed with water and dried over anhydrous Na$_2$SO$_4$, the solvent was removed and the resulting residue was purified by flash chromatography over silicagel (eluent:cyclohexane/ethylacetate 9:1). 20.7 g (82.5% of theory) of a threo/erythro-mixture of 1-(2,4-dichlorophenyl)-2-nitro-propan-1-ol was obtained. Crystallisation from cyclohexane yielded pure erythro 1-(2,4-dichlorophenyl)-2-nitro-propan-1-ol.

(erythro-form) $^1$H NMR (400 MHz, CDCl$_3$): δ 1.43 (d, 3H, CH$_3$), 2.92 (d, 1H$_2$OH), 4.84 (m, 1H, CH), 5.79 (t, 1H, CH), 7.34 (d, 1H, Ar—H), 7.40 (d, 1H, Ar—H), 7.59 (d, 1H, Ar—H).

b) Preparation of 2,4-dichloro-1-(1-fluoro-2-nitro-propyl)-benzene

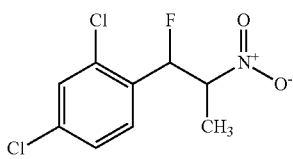

To a stirred mixture of erythro 1-(2,4-dichlorophenyl)-2-nitro-propan-1-ol (2.5 g, 10.0 mmol) in dry dichloromethane (20 ml) under nitrogen atmosphere DAST (1.3 ml, 10.0 mmol) in dichloromethane (5 ml) was added dropwise under cooling to 5° C. The solution was stirred at ambient temperature for 1 hour. Dichloromethane (80 ml) was added and the organic layer was washed sequentially with saturated NaHCO$_3$ (50 ml), 1M HCl (30 ml) and sole (30 ml). The organic layer was dried over NaSO$_4$, filtered, and concentrated. 2.5 g of 2,4-dichloro-1-(1-fluoro-2-nitro-propyl)-benzene was obtained in the form of a brown oil.

Example P28

Preparation of 1-(2,4,6-trichloro-phenyl)-propan-2-one

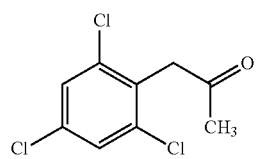

To the stirred solution of 1,3,5-trichloro-2-((E)-2-nitro-propenyl)-benzene (5 g, 18.72 mmol) in $H_2O$ (20 ml) and MeOH (60 ml), iron powder (2.355 g, 42.12 mmoles) and conc. HCl (11.5 ml, 112 mmol) was added at ambient temperature under nitrogen environment. The reaction mixture was stirred at 70° C. for 1 hour. After 1 hour additional iron powder (2.355 g, 42.12 mmoles) and conc. HCl (11.5 ml, 112 mmol) was added, while stirring was continued for 2 hours at 70° C. After completion of the reaction, (confirmed by TLC) reaction mass was cooled to ambient temperature and MeOH was evaporated. The resulting residue was diluted with water and extracted with ethyl acetate (3×80 ml). Combined ethyl acetate layer was washed with water and brine and dried over anhydrous $Na_2SO_4$. The organic layer was concentrated under vacuum. The crude material was purified by column chromatography (silicagel 60-120μ mesh, hexane/ethylacetate 95:5) to afford 3.7 g (83.3% of theory) of 1-(2,4,6-Trichloro-phenyl)-propan-2-one.

Tables 1 to 6: Compounds of Formula Ia:

The invention was further illustrated by the preferred individual compounds of formula (Ia) listed below in Tables 1 to 6. Characterising data are given in Table 9.

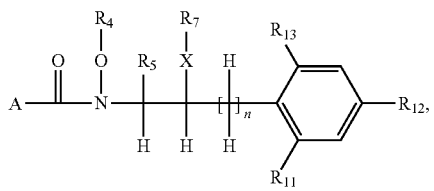

(Ia)

In the compounds of formula Ia, A is selected from the groups consisting of $A_1$, (A₁)

[structure showing pyrazole with $CF_2H$ and $CH_3$ groups]

$A_2$, (A₂)

[structure showing pyrazole with $CF_3$ and $CH_3$ groups]

and $A_3$, (A₃)

[structure showing pyrazole with $H_3C$, F and $CH_3$ groups]

and n is 0 or 1.

Each of Tables 1 to 6, which follow the Table Y below, comprises 100 compounds of the formula (Ia) in which $R_4$, $R_5$, $R_7$, X, $R_{11}$, $R_{12}$ and $R_{13}$ have the values given in Table Y and A has the value given in the relevant Table 1 to 6 and n has the value given in the relevant Table 1 to 6. Thus Table 1 corresponds to Table Y when Y is 1 and A has the value given under the Table 1 heading, Table 2 corresponds to Table Y when Y is 2 and A has the value given under the Table 2 heading, and so on for Tables 3 to 6.

In Tables 1 to 6 below "Me" stands for methyl, "Et" stands for ethyl, "i-Pr" stands for isopropyl, "c-Pr" stands for cyclopropyl and "t-Bu" stands for tertiary butyl.

TABLE Y

| Cpd No. | $R_4$ | $R_5$ | $R_7$ | X | $R_{11}$ | $R_{12}$ | $R_{13}$ |
|---|---|---|---|---|---|---|---|
| Y.001 | Me | Me | H | absent | H | Cl | H |
| Y.002 | Me | Me | H | absent | Cl | Cl | H |
| Y.003 | Me | Me | H | absent | Cl | Cl | Cl |
| Y.004 | Me | Me | H | absent | Cl | Br | Cl |
| Y.005 | Me | Me | H | absent | Cl | I | Cl |
| Y.006 | Me | Me | H | absent | Cl | Me | Cl |
| Y.007 | Me | Me | H | absent | Cl | $CHF_2$ | Cl |
| Y.008 | Me | Me | H | absent | Cl | $CF_3$ | Cl |
| Y.009 | Me | Me | H | absent | Cl | C≡CH | Cl |
| Y.010 | Me | Me | H | absent | Cl | t-Bu | Cl |
| Y.011 | Me | Me | H | absent | Cl | CH=$NOCH_3$ | Cl |
| Y.012 | Me | Me | H | absent | H | 4-Cl-phenyl | H |
| Y.013 | Me | Me | H | absent | Cl | 4-Cl-phenyl | H |
| Y.014 | Me | Me | H | absent | Cl | 4-Cl-phenyl | Cl |
| Y.015 | Me | Me | H | absent | H | 4-Cl-phenoxy | H |
| Y.016 | Me | Me | H | absent | Cl | 4-Cl-phenoxy | H |

TABLE Y-continued

| Cpd No. | R4 | R5 | R7 | X | R11 | R12 | R13 |
|---|---|---|---|---|---|---|---|
| Y.017 | Me | Me | H | absent | Cl | 4-Cl-phenoxy | Cl |
| Y.018 | Me | Me | H | absent | Me | Cl | H |
| Y.019 | Me | Me | H | absent | Me | Cl | Cl |
| Y.020 | Me | Me | H | absent | Me | Br | Cl |
| Y.021 | Me | Me | H | absent | Me | I | Cl |
| Y.022 | Me | Me | H | absent | Me | Me | Cl |
| Y.023 | Me | Me | H | absent | Me | Me | Me |
| Y.024 | Me | Me | H | absent | H | Br | H |
| Y.025 | Me | Me | H | absent | Br | Br | H |
| Y.026 | Me | Me | H | absent | Br | Br | Br |
| Y.027 | H | Me | H | absent | H | Cl | H |
| Y.028 | H | Me | H | absent | Cl | Cl | H |
| Y.029 | H | Me | H | absent | Cl | Cl | Cl |
| Y.030 | Et | Me | H | absent | H | Cl | H |
| Y.031 | Et | Me | H | absent | Cl | Cl | H |
| Y.032 | Et | Me | H | absent | Cl | Cl | Cl |
| Y.033 | i-Pr | Me | H | absent | Cl | Cl | H |
| Y.034 | CHF2 | Me | H | absent | Cl | Cl | H |
| Y.035 | CHF2 | Me | H | absent | Cl | Cl | Cl |
| Y.036 | CF3 | Me | H | absent | Cl | Cl | H |
| Y.037 | CF3 | Me | H | absent | Cl | Cl | Cl |
| Y.038 | Me | H | H | absent | H | Cl | H |
| Y.039 | Me | H | H | absent | Cl | Cl | H |
| Y.040 | Me | H | H | absent | Cl | Cl | Cl |
| Y.041 | Me | H | H | absent | Cl | Br | Cl |
| Y.042 | Me | H | H | absent | Cl | I | Cl |
| Y.043 | Me | H | H | absent | Cl | Me | Cl |
| Y.044 | Me | H | H | absent | H | 4-Cl-phenoxy | H |
| Y.045 | Me | H | H | absent | Cl | 4-Cl-phenoxy | H |
| Y.046 | Me | H | H | absent | Cl | 4-Cl-phenoxy | Cl |
| Y.047 | Me | H | H | absent | Me | Me | Cl |
| Y.048 | Me | H | H | absent | Me | Me | Me |
| Y.049 | Me | H | H | absent | H | Br | H |
| Y.050 | Me | H | H | absent | Br | Br | H |
| Y.051 | Me | H | H | absent | Br | Br | Br |
| Y.052 | H | H | H | absent | H | Cl | H |
| Y.053 | H | H | H | absent | Cl | Cl | H |
| Y.054 | H | H | H | absent | Cl | Cl | Cl |
| Y.055 | Me | H | Me | absent | Cl | Cl | H |
| Y.056 | Me | H | Me | absent | Cl | Cl | Cl |
| Y.057 | Me | H | Me | absent | H | t-Bu | H |
| Y.058 | Me | H | Et | absent | Cl | Cl | Cl |
| Y.059 | Me | H | n-Pr | absent | Cl | Cl | H |
| Y.060 | Me | H | n-Pr | absent | Cl | Cl | Cl |
| Y.061 | Me | Me | Me | O | H | Cl | H |
| Y.062 | Me | Me | Me | O | Cl | Cl | H |
| Y.063 | Me | Me | Me | O | Cl | Cl | Cl |
| Y.064 | Me | Me | Me | O | Cl | Br | Cl |
| Y.065 | Me | Me | Me | O | Cl | I | Cl |
| Y.066 | Me | Me | Me | O | Cl | Me | Cl |
| Y.067 | Me | Me | Me | O | Cl | CHF2 | Cl |
| Y.068 | Me | Me | Me | O | Cl | CF3 | Cl |
| Y.069 | Me | Me | Me | O | Cl | C≡CH | Cl |
| Y.070 | Me | Me | Me | O | H | 4-Cl-phenoxy | H |
| Y.071 | Me | Me | Me | O | Cl | 4-Cl-phenoxy | H |
| Y.072 | Me | Me | Me | O | Cl | 4-Cl-phenoxy | Cl |
| Y.073 | Me | Me | Me | O | Me | Me | Me |
| Y.074 | Me | Me | Me | O | Br | Br | Br |
| Y.075 | H | Me | Me | O | H | Cl | H |
| Y.076 | H | Me | Me | O | Cl | Cl | H |
| Y.077 | H | Me | Me | O | Cl | Cl | Cl |
| Y.078 | Me | Me | Et | O | H | Cl | H |
| Y.079 | Me | Me | Et | O | Cl | Cl | H |
| Y.080 | Me | Me | Et | O | Cl | Cl | Cl |
| Y.081 | Me | Me | CH2C≡CH | O | H | Cl | H |
| Y.082 | Me | Me | CH2C≡CH | O | Cl | Cl | H |
| Y.083 | Me | Me | CH2C≡CH | O | Cl | Cl | Cl |
| Y.084 | Me | Me | Me | S | H | Cl | H |
| Y.085 | Me | Me | Me | S | Cl | Cl | H |
| Y.086 | Me | Me | Me | S | Cl | Cl | Cl |
| Y.087 | Me | Me | Me | S | Cl | Br | Cl |
| Y.088 | Me | Me | Me | S | Cl | I | Cl |
| Y.089 | Me | Me | Me | S | Cl | Me | Cl |
| Y.090 | Me | Me | Me | S | Cl | CHF2 | Cl |
| Y.091 | Me | Me | Me | S | Cl | CF3 | Cl |
| Y.092 | Me | Me | Me | S | Cl | C≡CH | Cl |
| Y.093 | Me | Me | Me | S | H | 4-Cl-phenoxy | H |
| Y.094 | Me | Me | Me | S | Cl | 4-Cl-phenoxy | H |

TABLE Y-continued

| Cpd No. | R$_4$ | R$_5$ | R$_7$ | X | R$_{11}$ | R$_{12}$ | R$_{13}$ |
|---|---|---|---|---|---|---|---|
| Y.095 | Me | Me | Me | S | Cl | 4-Cl-phenoxy | Cl |
| Y.096 | Me | Me | CH$_2$C≡CH | S | Cl | Cl | H |
| Y.097 | Me | Me | CH$_2$C≡CH | S | Cl | Cl | Cl |
| Y.098 | H | Me | Me | S | H | Cl | H |
| Y.099 | H | Me | Me | S | Cl | Cl | H |
| Y.100 | H | Me | Me | S | Cl | Cl | Cl |

Table 1 provides 100 compounds of formula (Ia), wherein A is A$_1$

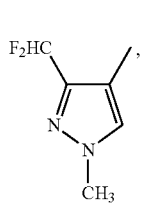
(A$_1$)

n is 0, and R$_4$, R$_5$, R$_7$, X, R$_{11}$, R$_{12}$ and R$_{13}$ are as defined in Table Y.

For example, compound 1.001 has the following structure:

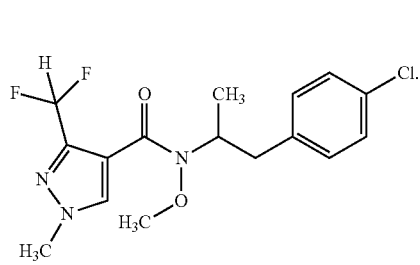
(1.001)

Table 2 provides 100 compounds of formula (Ia), wherein A is A$_1$

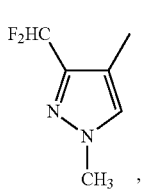
(A$_1$)

n is 1, and R$_4$, R$_5$, R$_7$, X, R$_{11}$, R$_{12}$ and R$_{13}$ are as defined in Table Y.

For example, compound 2.057 has the following structure:

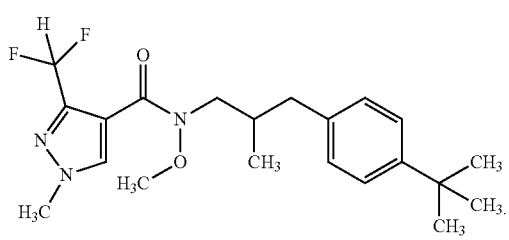
(2.057)

Table 3 provides 100 compounds of formula (Ia), wherein A is A$_2$

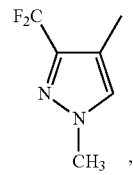
(A$_2$)

n is 0, and R$_4$, R$_5$, R$_7$, x, R$_{11}$, R$_{12}$ and R$_{13}$ are as defined in Table Y.

For example, compound 3.002 has the following structure:

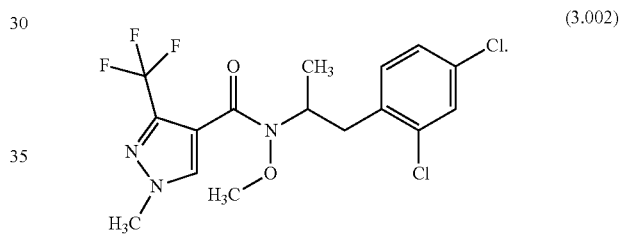
(3.002)

Table 4 provides 100 compounds of formula (Ia), wherein A is A$_2$

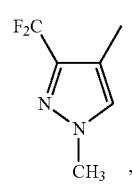
(A$_2$)

n is 1, and R$_4$, R$_5$, R$_7$, X, R$_{11}$, R$_{12}$ and R$_{13}$ are as defined in Table Y. For example, compound 4.003 has the following structure:

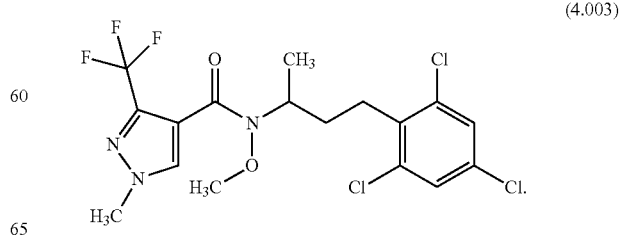
(4.003)

Table 5 provides 100 compounds of formula (Ia), wherein A is $A_3$

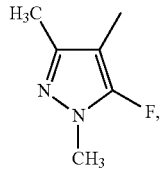
($A_3$)

n is 0, and $R_4$, $R_5$, $R_7$, X, $R_{11}$, $R_{12}$ and $R_{13}$ are as defined in Table Y. For example, compound 5.002 has the following structure:

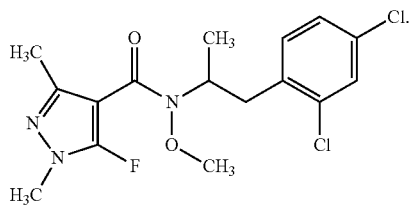
(5.002)

Table 6 provides 100 compounds of formula (Ia), wherein A is $A_3$

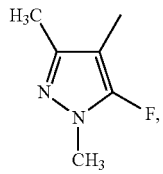
($A_3$)

n is 1, and $R_4$, $R_5$, $R_7$, X, $R_{11}$, $R_{12}$ and $R_{13}$ are as defined in Table Y. For example, compound 6.003 has the following structure:

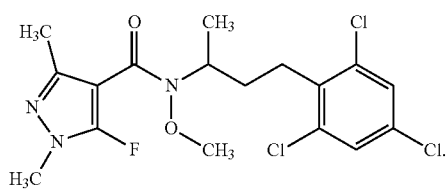
(6.003)

Tables 7 and 8:

Each of Tables 7 to 8, which follow the Table Y above, comprises 100 compounds of the formula (IIb) in which $R_4$, $R_5$, $R_7$, X, $R_{11}$, $R_{12}$ and $R_{13}$ have the values given in Table Y and n has the value given in the relevant Table 7 to 8. Thus Table 7 corresponds to Table Y when Y is 7, Table 8 corresponds to Table Y when Y is 8.

Table 7 provides 100 compounds of formula (IIb)

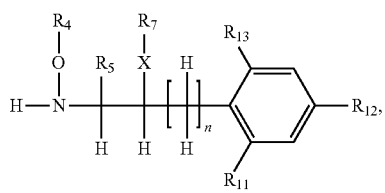
(IIb)

wherein n is 0, and $R_4$, $R_5$, $R_7$, X, $R_{11}$, $R_{12}$ and $R_{13}$ are as defined in Table Y.

For example, compound 7.001 has the following structure:

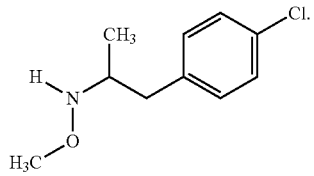
(7.001)

Table 8 provides 100 compounds of formula (IIb)

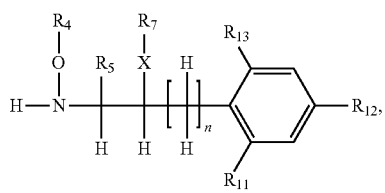
(IIb)

wherein n is 1, and $R_4$, $R_5$, $R_7$, X, $R_{11}$, $R_{12}$ and $R_{13}$ are as defined in Table Y.

Table 9: Characterising Data:

Table 9 shows selected melting point and selected NMR data for compounds of Table 1 to 6. $CDCl_3$ is used as the solvent for NMR measurements, unless otherwise stated. If a mixture of solvents is present, this is indicated as, for example: $CDCl_3/d_6$-DMSO). No attempt is made to list all characterising data in all cases.

In Table 9 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

m.p.=melting point
S=singlet
d=doublet
t=triplet
m=multiplet
b.p.=boiling point.
br=broad
dd=doublet of doublets
q=quartet
ppm=parts per million

TABLE 9

| Cpd No. | 1H-NMR data: ppm (multiplicity/number of Hs) | MS [M + H]+ | m.p. (° C.) | LCMS data |
|---|---|---|---|---|
| 1.001 | 1.33-1.37 (d, 3H); 2.77-2.82 (dd, 1H); 3.07-3.13 (dd, 1H); 3.64 (s, 3H); 3.94 (s, 3H); 4.63-4.68 (m, 1H); 6.98-7.28 (m, 5H); 7.61 (s, 1H). | 358/360 | oil | |
| 1.002 | 1.41-1.46 (d, 3H); 2.99-3.04 (dd, 1H); 3.17-3.23 (dd, 1H); 3.60 (s, 3H); 3.95 (s, 3H); 4.68-4.70 (m, 1H); 7.10-7.62 (m, 5H) | 392/394/396 | 98-102 | |
| 1.003 | 1.38-1.39 (d, 3H); 3.20-3.26 (dd, 1H); 3.32-3.37 (dd, 1H); 3.70 (s, 3H); 3.97 (s, 3H); 4.88-4.93 (m, 1H); 7.02-7.29 (t, 1H); 7.27 (s, 2H); 7.81 (s, 1H) | 426/428/430 | 110-112 | |
| 1.015 | 1.36-1.39 (d, 3H); 2.78-2.84 (dd, 1H); 3.05-3.12 (dd, 1H); 3.65 (s, 3H); 3.94 (s, 3H); 4.64-4.68 (m, 1H); 6.80-6.90 (m, 4H); 6.95-7.23 (t, 1H, $CHF_2$); 7.17-7.26 (m, 4H); 7.67 (s, 1H) | 450/452 | oil | |
| 1.028 | 1.40-1.41 (d, 3H); 2.89-2.94 (dd, 1H); 3.03-3.14 (dd, 1H); 3.86 (s, 3H); 4.3-4.5 ($m_{br}$, 1H); 6.5-7.0 ($m_{br}$, 2H); 7.19-7.21 (m, 2H); 7.36 (m, 1H); 7.8-8.6 ($m_{br}$, 1H) | 378/380/382 | | |
| 1.031 | 1.14-1.20 (t, 3H); 1.36-1.45 (2d, 3H); 2.98-3.03 (dd, 1H); 3.19-3.25 (dd, 1H); 3.74-3.82 (q, 3H); 3.94 (s, 3H); 4.64-4.70 (m, 1H); 6.93-7.65 (m, 5H) | 406/408/410 | 116-118 | |
| 1.032 | 1.20-1.24 (t, 3H); 1.35-1.37 (d, 3H); 3.23-3.28 (dd, 1H); 3.33-3.38 (dd, 1H); 3.84-3.88 (q, 2H); 3.96 (s, 3H); 4.86-4.91 (m, 1H); 7.01-7.25 (t, 1H); 7.28 (s, 2H); 7.83 (s, 1H) | 440/442/444 | 111-114 | |
| 1.033 | 0.91-0.93 + 1.11-1.13 (2d, 6H); 1.42-1.48 (2d, 3H); 3.00-3.07 (dd, 1H); 3.29-3.36 (dd, 1H); 3.92 (s, 3H); 3.97-4.36 (m, 1H); 4.36-4.45 (m, 1H); 6.97-7.59 (m, 5H) | 420/422/424 | oil | |
| 1.059 | 0.84-0.87 (t, 3H); 1.14-1.25 (m, 2H); 1.61-1.69 (m, 2H); 3.55 (s, 3H); 3.71-3.80 (m, 1H); 3.80-3.84 (dd, 1H); 3.96 (s, 3H); 3.99-4.05 (dd, 1H); 7.07-7.36 (m, 4H); 7.79 (s, 1H) | 420/422/424 | oil | |
| 2.003 | 1.41 (d, 3H, CH3), 1.71-1.80 (m, 1H, CH2), 1.94-2.04 (m, 1H, CH2), 1.87-1.92 (m, 2H, CH2), 3.78 (s, 3H, CH3), 3.98 (s, 3H, CH3), 4.66-4.71 (m, 1H, CH), 7.11 (t, 1H, CHF2), 7.28 (s, 2H, Ar—H), 7.88 (s, 1H, pyrazole-H) | 440/442/444/446 | resin | |
| 2.040 | 1.89-1.96 (m, 2H, CH2), 2.91-2.95 (m, 2H, CH2), 3.66 (s, 3H, CH3), 3.83-3.86 (t, 2H, CH2), 3.97 (s, 3H, CH3), 7.31 (t, 1H, CHF2), 7.28 (s, 2H, Ar—H), 7.89 (s, 1H, pyrazole-H) | 426/428/430/432 | 95-96 | |
| 2.057 | 0.90-0.95 (d, 3H); 1.30 (s, 9H); 2.24-2.36 (m, 1H); 2.39-2.45 (dd, 1H); 2.67-2.72 (dd, 1H); 3.58 (s, 3H); 3.68-3.70 (d, 2H); 3.98 (s, 3H); 7.09-7.11 (d, 2H); 7.15-7.42 (m, 3H); 7.90 (s, 1H) | 394 | resin | |
| 7.001 | 1.02-1.06 (d, 3H); 2.54-2.59 (dd, 1H); 2.79-2.84 (dd, 1H); 3.14-3.24 (m, 1H), 3.52 (s, 3H); 5.3-5.5 ($s_{br}$, 1H); 7.12-7.16 (m, 2H); 7.25-7.28 (m, 2H). | 200/202 | liquid | |
| 7.002 | 1.04-1.09 (d, 3H); 2.66-2.71 (dd, 1H); 2.93-2.99 (dd, 1H); 3.25-3.33 (m, 1H), 3.52 (s, 3H); 5.2-5.4 ($s_{br}$, 1H); 7.17-7.18 (m, 2H); 7.35 (d, 1H) | 234/236/238 | liquid | |
| 7.015 | 1.07-1.09 (d, 3H); 2.53-2.62 (dd, 1H); 2.72-2.81 (dd, 1H); 3.16-3.26 (m, 1H), 3.54 (s, 3H); 5.3-5.5 ($s_{br}$, 1H); 6.86-6.94 (m, 4H); 7.14-7.18 (m, 2H); 7.24-7.29 (m, 2H) | 292/294 | liquid | |
| 7.028 | 1.08-1.11 (d, 3H); 2.69-2.74 (dd, 1H); 2.98-3.03 (dd, 1H); 3.24-3.32 (m, 1H); 5.3-5.6 ($s_{br}$, 1H); 7.18-7.19 (m, 2H); 7.39 (m, 1H); 7.5-8.2 ($s_{br}$, 1H) | 220/222/224 | 83-86 | |
| 7.031 | 0.98-1.02 + 1.08-1.12 (2d, 3H); 1.13-1.18 (2t, 3H); 2.63-2.68 + 2.70-2.78 (2dd, 1H); 2.94-3.10 + 3.15-3.21 (m, 1H), 3.25-3.31 + 3.71-3.78 (2q, 2H); 5.0-5.5 ($s_{br}$, 1H); 7.16-7.19 (m, 2H); 7.34-7.36 (m, 1H) | 248/250/252 | liquid | |

TABLE 9-continued

| Cpd No. | 1H-NMR data: ppm (multiplicity/number of Hs) | MS [M + H]$^+$ | m.p. (° C.) | LCMS data |
|---|---|---|---|---|
| 7.033 | 1.03-1.07 (d, 3H); 1.13-1.19 (m, 6H); 2.61-2.68 + 2.94-3.03 (2dd, 2H); 3.21-3.31 (m, 1H), 3.78-3.84 (m, 1H); 5.2 (s$_{br}$, 1H); 7.14-7.18 (m, 2H); 7.35-7.36 (m, 1H) | 262/264/266 | liquid | |
| 7.059 | 0.82-0.89 (t, 3H); 1.12-1.27 (m, 2H); 1.49-1.58 (m, 1H); 1.63-1.72 (m, 1H); 3.05-3.10 (dd, 1H); 3.12-3.18 (dd, 1H); 3.47 (s, 3H), 3.50-3.51 (m, 1H); 5.0-5.50 (s$_{br}$, 1H); 7.14-7.16 (m, 1H); 7.21-7.25 (m, 1H); 7.37-7.39 (m, 1H) | 262/264/266 | liquid | |
| 8.003 | 1.21 (d, 3H, CH$_3$), 1.52-1.59 (m, 1H, CH$_2$), 1.68-1.76 (m, 1H, CH$_2$), 2.80-2.83 (m, 2H, CH$_2$), 3.06-3.13 (m, 1H, CH), 1.45 (s, 1H, NH), 7.29 (s, 2H, Ar—H) | | liquid | |
| 8.040 | 1.74-1.82 (m, 2H, CH$_2$), 2.92-3.01 (m, 4H, CH2—CH2), 3.55 (s, 3H, CH$_3$), 5.60 (s, 1H, NH), 7.29 (s, 2H, Ar—H) | | liquid | |
| 8.057 | | 236 | liquid | |

Formulation examples for compounds of formula I:

Example F-1.1 to F-1.2

Emulsifiable Concentrates

| Components | F-1.1 | F-1.2 |
|---|---|---|
| compound of Tables 1-6 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1-6 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1-6 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1-6 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1-6 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1-6 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1-6 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Action

Example B-1

Action Against *Botrytis cinerea*—Fungal Growth Assay

Conidia of the fungus from cryogenic storage was directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition). Compounds 1.001, 1.002, 1.003, 1.015, 1.031, 1.032, 1.059 and 2.003 show very good activity in this test ($\leq 80\%$ inhibition).

Example B-2

Action Against *Mycosphaerella arachidis* (Early Leaf Spot of Groundnut; *Cercospora arachidicola* [Anamorph])—Fungal Growth Assay Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 6-7 days. The activity of a compound was expressed as fungal growth inhibition (0=no growth inhibition, ratings of 80% to 99% mean good to very good inhibition, 100%=complete inhibition). Compounds 1.001, 1.002, 1.003, 1.015, 1.031, 1.032, 1.059, 2.003 and 1.057 show very good activity in this test ($\leq 80\%$ inhibition).

Example B-3

Action Against *Septoria tritici*—Fungal Growth Assay

Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was determined photometrically after 72 hrs. The activity of a compound was expressed as fungal growth inhibition (0=no growth inhibition, ratings of 80% to 99% mean good to very good inhibition, 100%=complete inhibition). Compounds 1.001, 1.002, 1.003, 1.015, 1.031, 1.032, 1.059, 2.003 and 1.057 show very good activity in this test ($\leq 80\%$ inhibition).

Example B-4

Action against *Tapesia yallundae*—Fungal Growth Assay

Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 6-7 days. The activity of a compound was expressed as fungal growth inhibition (0=no growth inhibition, ratings of 80% to 99% mean good to very good inhibition, 100%=complete inhibition).

Compound 1.001 shows very good activity in this test (≦80% inhibition).

Example B-5

Action Against *Monographella nivalis* (Anamorph: *Fusarium nivale, Microdochium nivale*; Snow Mould)—Fungal Growth Assay Conidia of the fungus from cryogenic storage were directly mixed into nutrient broth (PDB potato dextrose broth). After placing a DMSO-solution of the test compounds (0.002% active ingredient) into a microtiter plate (96-well format) the nutrient broth containing the fungal spores was added. The test plates were incubated at 24° C. and the inhibition of growth was measured photometrically after 72 hrs (0=no growth inhibition, ratings of 80% to 99% mean good to very good inhibition, 100%=complete inhibition).

Compounds 1.001, 1.002, 1.003, 1.015, 1.031, 1.032, 1.059 and 2.003 show very good activity in this test (≦80% inhibition).

Compound 1.057 shows good activity in this test (≦50% inhibition).

Example B-6

Action Against *Rhizoctonia solani*—Fungal Growth Assay

Mycelial fragments of a newly grown liquid culture of the fungus were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition).

Compound 2.003 shows very good activity in this test (≦80% inhibition).

Compound 1.003 shows good activity in this test (≦50% inhibition).

Example B-7

Action Against *Erysiphe graminis* f. Sp. Tritici (Wheat Powdery Mildew)

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 7 days after inoculation as preventive fungicidal activity.

Compounds 1.001, 1.002, 1.003, 1.015, 1.031, 1.032, 1.033, 1.059 and 2.003 show very good activity in this test (≦80% inhibition).

Example B-8

Protective Action Against *Puccinia recondita* (Brown Rust) on Wheat

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 8 days after inoculation as preventive fungicidal activity.

Compounds 1.001, 1.002, 1.003, 1.015, 1.059 and 2.003 show very good activity in this test (≦80% inhibition).

Compounds 1.032 and 1.057 show good activity in this test (≦50% inhibition).

Example B-9

Curative Action Against *Puccinia recondita* (Brown Rust) on Wheat

Wheat leaf segments were placed on agar in multiwell plates (24-well format) and inoculated with a spore suspension of the fungus. One day after inoculation the leaf segments were sprayed with test solutions (0.02% active ingredient). After appropriate incubation the activity of a compound was assessed 8 days after inoculation as curative fungicidal activity.

Compounds 1.002 and 1.003 show very good activity in this test (≦80% inhibition). Compound 1.015 shows good activity in this test (≦50% inhibition).

Example B-10

Action Against *Pyrenophora teres* (Net Blotch) on Barley

Barley leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 4 days after inoculation as preventive fungicidal activity.

Compounds 1.001, 1.002, 1.003, 1.015, 1.031, 1.032, 1.033, 1.059 and 1.057 show very good activity in this test (≦80% inhibition).

What is claimed is:
1. A compound of formula I

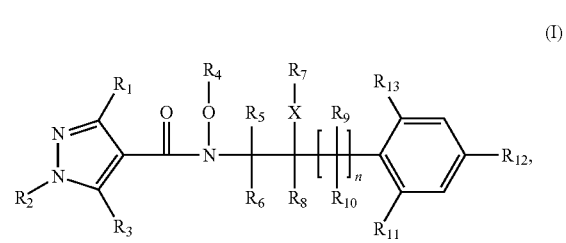

(I)

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$, $R_6$, $R_8$, $R_9$ and $R_{10}$ are, independently from each other, hydrogen, halogen, $C_1$-$C_4$alkyl or $C_1$-$C_4$haloalkyl;

$R_7$ is hydrogen, halogen, $C_1$-$C_4$alkyl, $C_2$-$C_6$alkenyl or $C_3$-$C_6$alkinyl;

$R_{11}$ is hydrogen, halogen or $C_1$-$C_6$alkyl;

$R_{12}$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C(C_1$-$C_4$alkyl)=NO—$C_1$-$C_4$alkyl, $C_1$-$C_6$haloalkyl, $C_1$-$C_6$haloalkoxy, $C_2$-$C_6$haloalkenyl, or $C_2$-$C_6$haloalkenyloxy;

$R_{13}$ is hydrogen, halogen, $C_1$-$C_6$alkyl;

X is oxygen, sulfur or absent; with the proviso that $R_7$ is different from halogen if X is oxygen or sulfur;

n is 0 or 1; and agronomically acceptable salts/stereoisomers/diastereoisomers/enantiomers/tautomers and N-oxides thereof.

2. A compound according to claim 1, wherein $R_1$ is difluoromethyl, trifluoromethyl or methyl.

3. A compound according to claim 1, wherein $R_2$ is methyl.

4. A compound according to claim 1, wherein $R_3$ is hydrogen or fluoro.

5. A compound according to claim 1, wherein $R_4$ is hydrogen, methyl or ethyl.

6. A compound according to claim 1, wherein $R_4$ is methyl.

7. A compound according to claim 1, wherein $R_5$ is hydrogen or methyl.

8. A compound according to claim 1, wherein n is 0.

9. A compound according to claim 1, wherein X is oxygen.

10. A compound according to claim 1, wherein $R_8$, $R_9$ and $R_{10}$ are hydrogen.

11. A compound according to claim 1, wherein $R_{11}$, $R_{12}$ and $R_{13}$ is hydrogen or chloro.

12. A compound according to claim 1, wherein $R_{12}$ is chloro or $C_1$-$C_4$alkyl.

13. A method of controlling infestation of useful plants by phytopathogenic microorganisms, wherein a compound of formula I according to claim 1 or a composition, comprising this compound as active ingredient, is applied to the plants, to parts thereof or the locus thereof.

14. A composition for controlling and protecting against phytopathogenic microorganisms, comprising a compound of formula I according to claim 1 and an inert carrier.

* * * * *